US012383661B2

(12) United States Patent
Ochiai et al.

(10) Patent No.: US 12,383,661 B2
(45) Date of Patent: Aug. 12, 2025

(54) MANUAL BREAST PUMP

(71) Applicant: PIGEON CORPORATION, Tokyo (JP)

(72) Inventors: Yukifumi Ochiai, Tokyo (JP); Sumiko Kuroishi, Tokyo (JP); Katsutoshi Takahashi, Tokyo (JP); Yoshihito Sugiyama, Tokyo (JP)

(73) Assignee: PIGEON CORPORATION, Tokyo (JP)

( * ) Notice: Subject to any disclaimer, the term of this patent is extended or adjusted under 35 U.S.C. 154(b) by 760 days.

(21) Appl. No.: 16/621,950

(22) PCT Filed: Jun. 22, 2018

(86) PCT No.: PCT/JP2018/023869
§ 371 (c)(1),
(2) Date: Dec. 12, 2019

(87) PCT Pub. No.: WO2019/004092
PCT Pub. Date: Jan. 3, 2019

(65) Prior Publication Data
US 2020/0171223 A1 Jun. 4, 2020

(30) Foreign Application Priority Data
Jun. 30, 2017 (JP) ................. 2017-128897

(51) Int. Cl.
*A61M 1/06* (2006.01)
*A61M 1/00* (2006.01)
(52) U.S. Cl.
CPC .............. *A61M 1/06* (2013.01); *A61M 1/064* (2014.02); *A61M 1/82* (2021.05)
(58) Field of Classification Search
CPC .......... A61M 1/007; A61M 2210/1007; A61M 1/06; A61M 1/062; A61M 1/064;
(Continued)

(56) References Cited

U.S. PATENT DOCUMENTS 6,749,582 B2 6/2004 Britto
2005/0154348 A1* 7/2005 Lantz .................. A61M 1/0697
604/74
(Continued)

FOREIGN PATENT DOCUMENTS

CN 201436036 U 4/2010
CN 104918642 A 9/2015
(Continued)

OTHER PUBLICATIONS

Written opinion of PCT/JP2018/023869 mailed Aug. 21, 2018.
(Continued)

*Primary Examiner* — Kevin C Sirmons
*Assistant Examiner* — William R Frehe
(74) *Attorney, Agent, or Firm* — Muncy, Geissler, Olds & Lowe, P.C.

(57) ABSTRACT

[Problem] To provide a manual breast pump in which a muscle load due to a repeated operation of a handle can be reduced, and in which a section contacting breast milk can be cleaned easily.
[Solution] A manual breast pump includes a main body casing 31, a hood 4, a base part 32 which is held by the main body casing 31 and has a communicating part S4 connected spatially to an inner space S3, a diaphragm generating a negative pressure in the communicating part S4, a holding member 33 which is provided at the base part 32 and includes a wall part sandwiched between the main body casing 31 and the base part 32, and a handle 5 which is provided to be rotatable with respect to the main body casing 31 with an axis 325 of the base part 32 as the center, and is for an operation of deforming the diaphragm 34. When the handle 5 rotates with respect to the main body casing 31 with the axis 325 of the base part 32 as the center, the base part
(Continued)

32 rotates with the handle 5 with respect to the main body casing 31 with the holding member 33 interposed.

12 Claims, 9 Drawing Sheets

(58) Field of Classification Search
CPC ...... A61M 1/066; A61M 1/068; A61M 1/067; A61M 1/069; A61M 1/0693; A61M 1/06935; A61M 1/0697; A61B 2018/00333; A61J 13/00
See application file for complete search history.

(56) References Cited

U.S. PATENT DOCUMENTS

2014/0094747 A1\* 4/2014 Hirata ................. A61M 1/06
604/74
2014/0100520 A1\* 4/2014 Yamashita ............. A61M 1/06
604/74
2015/0335800 A1 11/2015 Yamashita

FOREIGN PATENT DOCUMENTS

| JP | S63-147471 A | 6/1988 |
| JP | S63-252161 A | 10/1988 |
| WO | 2014/112078 A1 | 7/2014 |

OTHER PUBLICATIONS

English Translation of International Search Report of PCT/JP2018/023869 mailed Aug. 21, 2018.
Written opinion of PCT/JP2018/023869 mailed Aug. 21, 2018 and English translation thereof.
The office action of the corresponding CN application No. 201880042432.5 mailed Apr. 28, 2022 and machine English translation thereof.

\* cited by examiner

FIG. 3A
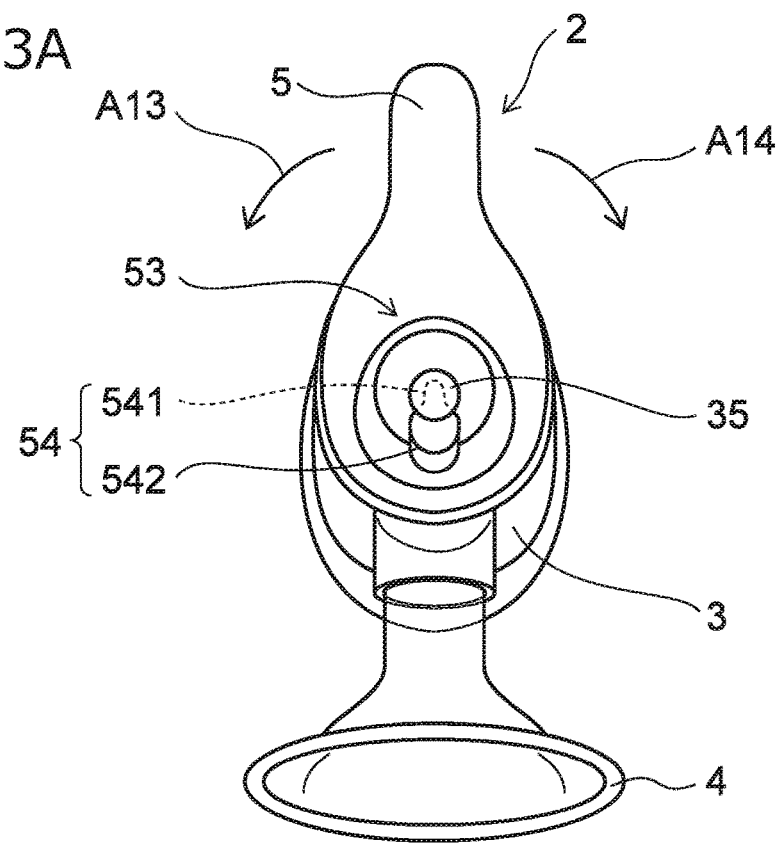
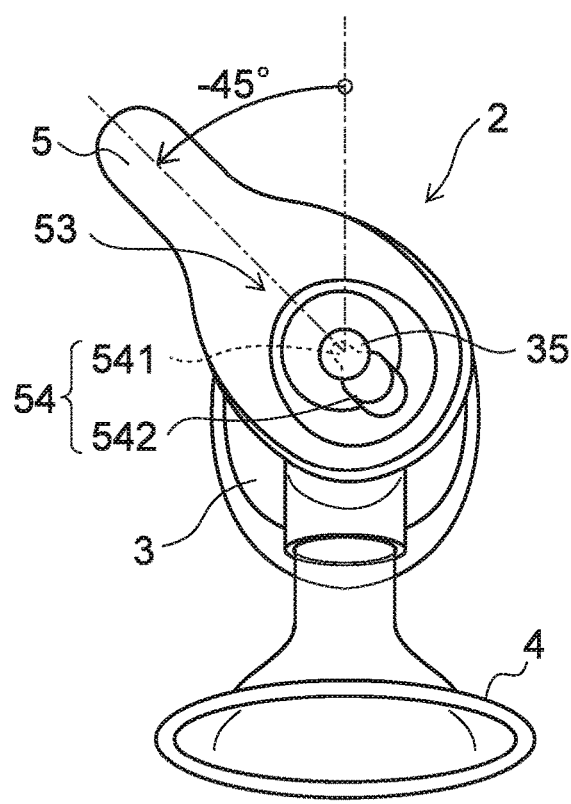
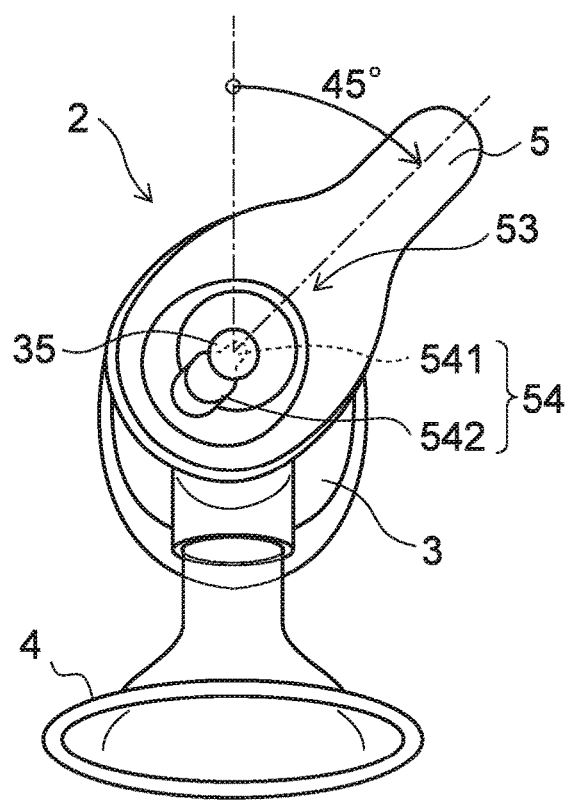
FIG. 3B
FIG. 3C

MANUAL BREAST PUMP

TECHNICAL FIELD

The invention relates to a manual breast pump for manually expressing breast milk.

BACKGROUND ART

Conventionally, a manual breast pump is known by which a user manually expresses breast milk. Generally, the manual breast pump includes a main body, a hood connected to the main body and fitted to a breast, a diaphragm which is connected to the main body and generates a negative pressure in an inner space of the hood, and a handle for an operation of deforming the diaphragm by approaching and moving away from the main body. Generally, the orientation of the handle with respect to the main body is fixed. That is, the handle has a back and forth motion of approaching and moving away from the main body in a state in which the orientation with respect to the main body is fixed. Therefore, when the user expresses breast milk by using the manual breast pump, the orientation of the handle is determined necessarily when the hood is fitted to the breast. Thereby, the user may not be able to place the joints of the hand operating the handle at an intermediate position. Therefore, there is room for improvement regarding the muscle load caused by the repeated operation of the handle.

Here, a manual breast pump discussed in Patent Literature 1 includes a suction cup forming an inner suction chamber, abreast shield spreading from the suction cup, and a manual operation lever provided at the suction cup. In the manual breast pump recited in Patent Literature 1, the manual operation lever is oriented at multiple positions with respect to the suction cup, and can be operated cyclically at each of the multiple positions to generate a negative pressure in the inner suction chamber. Also, the manual operation lever is rotatable with respect to the suction cup.

CITATION LIST

Patent Literature

[Patent Literature 1]
U.S. Pat. No. 6,749,582 specification

SUMMARY OF INVENTION

Problem to be Solved by the Invention

However, there is a problem in that the rotation mechanism of the manual operation lever is complex. Because the rotation mechanism is complex, it is difficult to clean the section contacted by the breast milk. Therefore, a manual breast pump is desirable in which the muscle load due to the repeated operation of the handle can be reduced, and the section contacted by the breast milk can be cleaned easily.

The invention is directed to solve these problems and provide a manual breast pump in which the muscle load due to the repeated operation of the handle can be reduced, and the section contacted by the breast milk can be cleaned easily.

Means for Solving the Problem

According to the invention, the problems are solved by a manual breast pump including a main body casing having an inner space where breast milk is collected temporarily, a hood connected to the main body casing and fitted to a breast, a base part which is held by the main body casing and has a communicating part connected spatially to the inner space, a diaphragm generating a negative pressure in the communicating part and being provided at the base part, a holding member which is provided at one of the main body casing or the base part and includes a wall part sandwiched between the main body casing and the base part, and a handle which is connected to the base part, is provided to be rotatable with respect to the main body casing with an axis of the base part as a center, and is for an operation of deforming the diaphragm, wherein when the handle rotates with respect to the main body casing with the axis of the base part as the center, the base part rotates with the handle with respect to the main body casing with the holding member interposed.

According to the configuration, the manual breast pump includes the base part which has the communicating part connected spatially to the inner space of the main body casing and is a member separate from the main body casing having the inner space where the breast milk is collected temporarily. The wall part of the holding member is sandwiched between the main body casing and the base part. Also, when the handle for the operation of deforming the diaphragm rotates with respect to the main body casing with the axis of the base part as the center, the base part rotates with the handle with respect to the main body casing with the holding member interposed. In other words, the handle is connected to the base part held by the main body casing via the holding member, and can rotate with the base part with respect to the main body casing with the axis of the base as the center. Therefore, the user can freely adjust the position (the angle) of the handle with respect to the main body casing when the hood is fitted to the breast; and the joints of the hand operating the handle can be placed at an intermediate position. The muscle load due to the repeated operation of the handle can be reduced thereby.

Also, the base part is provided as a member separate from the main body casing, and can rotate with respect to the main body casing while being held by the main body casing by means of the holding member. Therefore, a complex rotation mechanism rotating the handle is unnecessary; and a circular tubular or cup-shaped member including a wall part having a height sufficient to surround the periphery of the space where the negative pressure is applied is unnecessary. Therefore, the internal structure of the manual breast pump such as the section contacted by the breast milk, etc., can be simplified. Thereby, the user easily can clean the section contacted by the breast milk by disassembling the main body casing and the base part from each other.

Favorably, the main body casing includes a regulator regulating a range of the rotation of the base part with the axis of the base part as the center.

According to the configuration, the main body casing includes the regulator regulating the range of the rotation of the base part with the axis of the base part as the center. Therefore, the range of the rotation of the handle rotating with the base part is regulated by the regulator of the main body casing. In other words, the range of the rotation of the handle is limited to a prescribed range. Thereby, the range of the rotation of the handle is clear; and the user can adjust the handle with peace of mind to any position after ascertaining the rotation range of the handle.

Favorably, the holding member has a holding structure which protrudes from a surface of the wall part toward one of the main body casing or the base part and supports the holding of the base part by the main body casing.

According to the configuration, the holding member has the holding structure protruding from the surface of the wall part of the holding member toward one of the main body casing or the base part. The holding structure supports the holding of the base part by the main body casing. In other words, the holding structure supports the holding of the base part by the main body casing by the structure protruding from the surface of the wall part of the holding member. Thereby, the detachment of the base part from the main body casing can be suppressed even when the force due to the handle operation is applied in a direction oblique to the base part connected to the handle.

Favorably, the holding structure includes a first protrusion extending in a circumferential direction of the wall part, and a second protrusion which is provided to be separated from the first protrusion and extends in the circumferential direction of the wall part.

According to the configuration, the holding structure includes the first protrusion and the second protrusion. The first protrusion extends in the circumferential direction of the wall part of the holding member. The second protrusion is provided to be separated from the first protrusion and extends in the circumferential direction of the wall part. Therefore, the holding member can support the holding of the base part by the main body casing by the first protrusion and the second protrusion provided to be separated from each other. In other words, the holding member can receive, at the first protrusion and the second protrusion provided to be separated from each other, the force applied to the base part due to the handle operation. Thereby, the detachment of the base part from the main body casing can be suppressed more reliably even when the force due to the handle operation is applied in a direction oblique to the base part connected to the handle.

Favorably, the holding structure further includes a third protrusion which is provided between the first protrusion and the second protrusion and extends in the circumferential direction of the wall part.

According to the configuration, the third protrusion that extends in the circumferential direction of the wall part of the holding member is provided between the first protrusion and the second protrusion. Therefore, the third protrusion which is provided between the first protrusion and the second protrusion can ensure the sealability between the main body casing and the base part even when the force due to the handle operation is applied in a direction oblique to the base part connected to the handle.

Favorably, one of the main body casing or the base part where the holding member is provided includes a first supporter which protrudes toward the first protrusion and is provided at a position corresponding to the first protrusion at a side opposite to a side where the first protrusion protrudes, and a second supporter which protrudes toward the second protrusion and is provided at a position corresponding to the second protrusion at a side opposite to a side where the second protrusion protrudes.

According to the configuration, one of the main body casing or the base part where the holding member is provided includes the first supporter and the second supporter. The first supporter is provided at a position corresponding to the first protrusion at a side opposite to the side where the first protrusion protrudes. Therefore, the first supporter can support the first protrusion from the backside in a state in which the wall part of the holding member is sandwiched between the main body casing and the base part. Also, the second supporter is provided at a position corresponding to the second protrusion at a side opposite to the side where the second protrusion protrudes. Therefore, the second supporter can support the second protrusion from the backside in the state in which the wall part of the holding member is sandwiched between the main body casing and the base part. Thereby, the holding force of the base part by the main body casing can be increased; and the sealability between the main body casing and the base part can be increased.

Favorably, the length of the protrusion of one of the first supporter or the second supporter is longer than the length of the protrusion of the other of the first supporter or the second supporter.

According to the configuration, the length of the protrusion of one of the first supporter or the second supporter is longer than the length of the protrusion of the other of the first supporter or the second supporter. That is, the protruding length of the first supporter is different from the protruding length of the second supporter. Therefore, the holding force of the base part by the main body casing can be suppressed from becoming excessively high. Thereby, the mutual disassembleability of the main body casing and the base part can be increased while maintaining the holding force of the base part by the main body casing.

Favorably, the holding member includes a hook part that catches on at least one of the first supporter or the second supporter.

According to the configuration, at least one of the first supporter or the second supporter catches on the hook part provided in the holding member. Therefore, the detachment of the holding member from the base part or the main body casing can be suppressed even when a relatively strong force is applied to the holding member.

Favorably, the holding member includes a bottom part which has a through-hole spatially connecting the inner space and the communicating part, and a backflow prevention wall which surrounds a periphery of the through-hole and extends outward from the bottom part.

According to the configuration, the holding member includes the backflow prevention wall. The backflow prevention wall surrounds the periphery of the through-hole provided in the bottom part of the holding member and extends outward from the bottom part. Therefore, the expressed breast milk can be suppressed from traveling along the wall part and/or the bottom part of the holding member and being suctioned through the through-hole of the bottom part toward the communicating part. That is, the backflow prevention wall can suppress the flow (the backward flow) of the expressed breast milk via the through-hole of the bottom part toward the communicating part.

Effects of the Invention

According to the invention, a manual breast pump can be provided in which the muscle load due to the repeated operation of the handle can be reduced, and the section contacted by the breast milk can be cleaned easily.

BRIEF DESCRIPTION OF DRAWINGS

FIG. 3 is a plan view illustrating states of the handle of the embodiment rotating.

MODES FOR CARRYING OUT THE INVENTION

Figure 1:
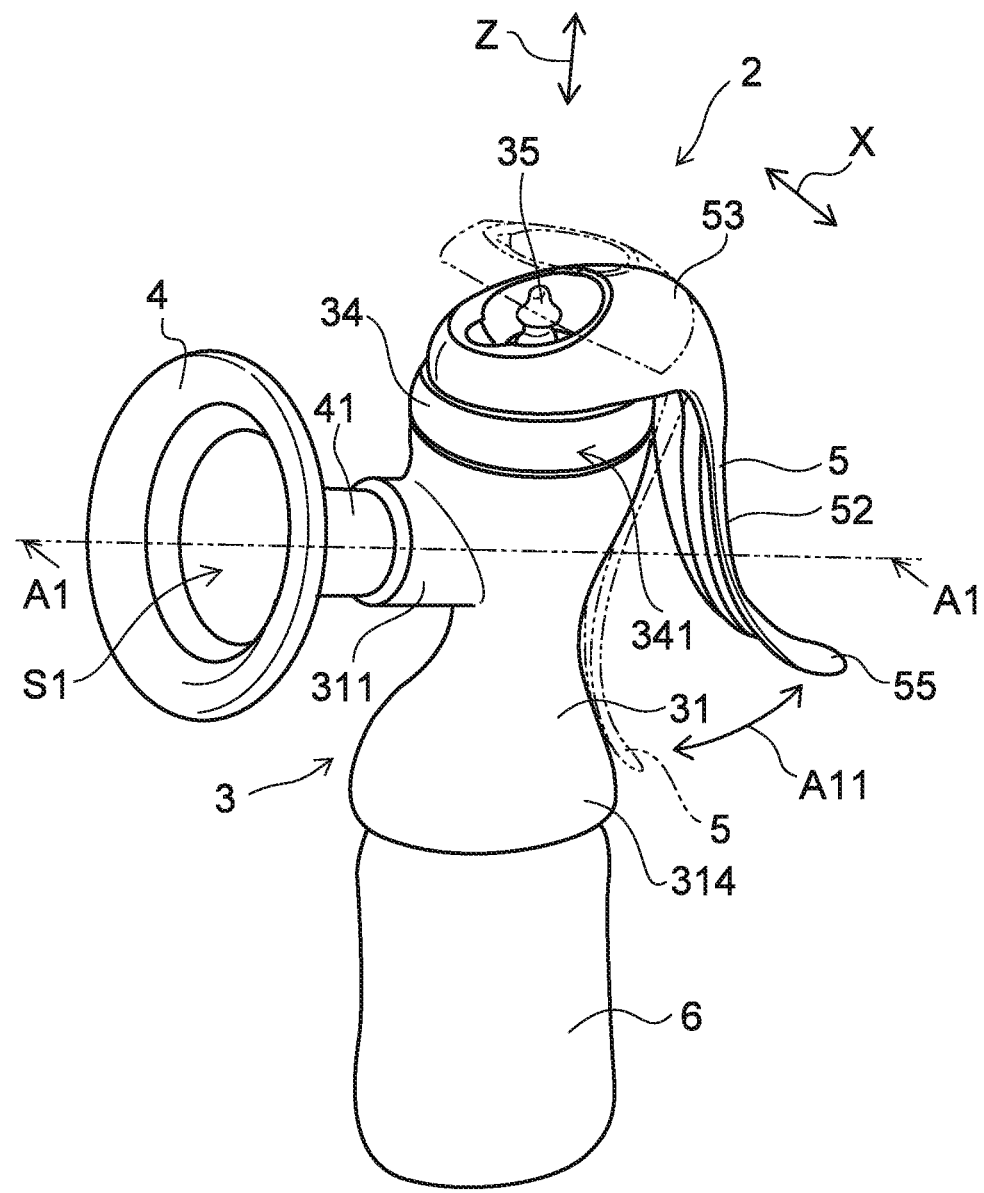
FIG. 1 is a perspective view illustrating a manual breast pump according to an embodiment of the invention.

Favorable embodiments of the invention will now be described in detail with reference to the drawings.

Because the embodiments described below are favorable specific examples of the invention, various favorable technical limits are provided; but the scope of the invention is not limited to these aspects unless the invention is particularly and expressly limited in the following description. Also, similar components in the drawings are marked with the same reference numerals; and a detailed description is omitted as appropriate.

Figure 4:
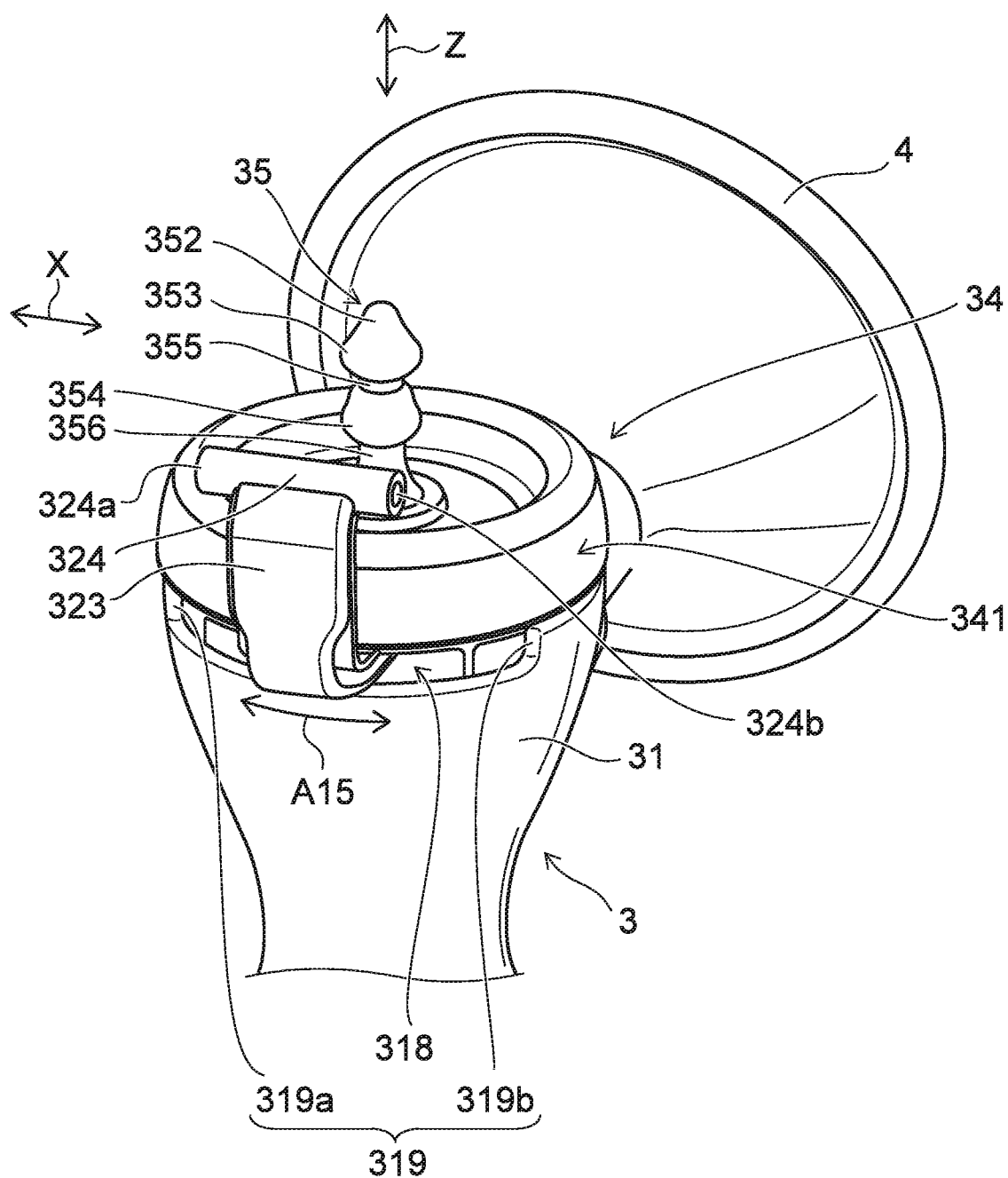
FIG. 4 is an enlarged view illustrating the vicinity of an arm of the embodiment.

A manual breast pump according to an embodiment of the invention will now be described with reference to FIG. 1 to FIG. 4. In FIG. 4, a handle 5 is not illustrated for convenience of description. The manual breast pump (for convenience of description in the description recited below, called simply the "breast pump") 2 illustrated in FIG. 1 to FIG. 4 is an implement which the user can manually operate to express breast milk, and which is used when it is difficult to give breast milk directly to an infant, when the nipple is injured, when preventing mastitis, etc. The user uses the breast pump 2 by holding the breast pump 2 in the user's own hand. Therefore, it is favorable for the breast pump 2 to be lightweight, to be operatable with one hand, and to be such that fatigue can be reduced.

The breast pump 2 includes a main body 3, a hood 4, the handle 5, and a bottle 6. The hood 4 is formed in a bugle-mouth configuration or a substantially dome configuration corresponding to the shape of a breast and is fitted to the breast. A reduced-diameter part 41 of the hood 4 where the diameter is smallest is connected to a mounting part 311 provided at the upper part of a casing (a main body casing) 31 of the main body 3. The casing 31 of the embodiment corresponds to the "main body casing" of the invention. A space S1 which is surrounded with the hood 4 has a receiving space S2 which receives the nipple of the user to airtightly seal the nipple when the user inserts the breast into the space S1. A structure which can express breast milk is formed by setting the interior of the receiving space S2 to a negative pressure.

Figure 2:
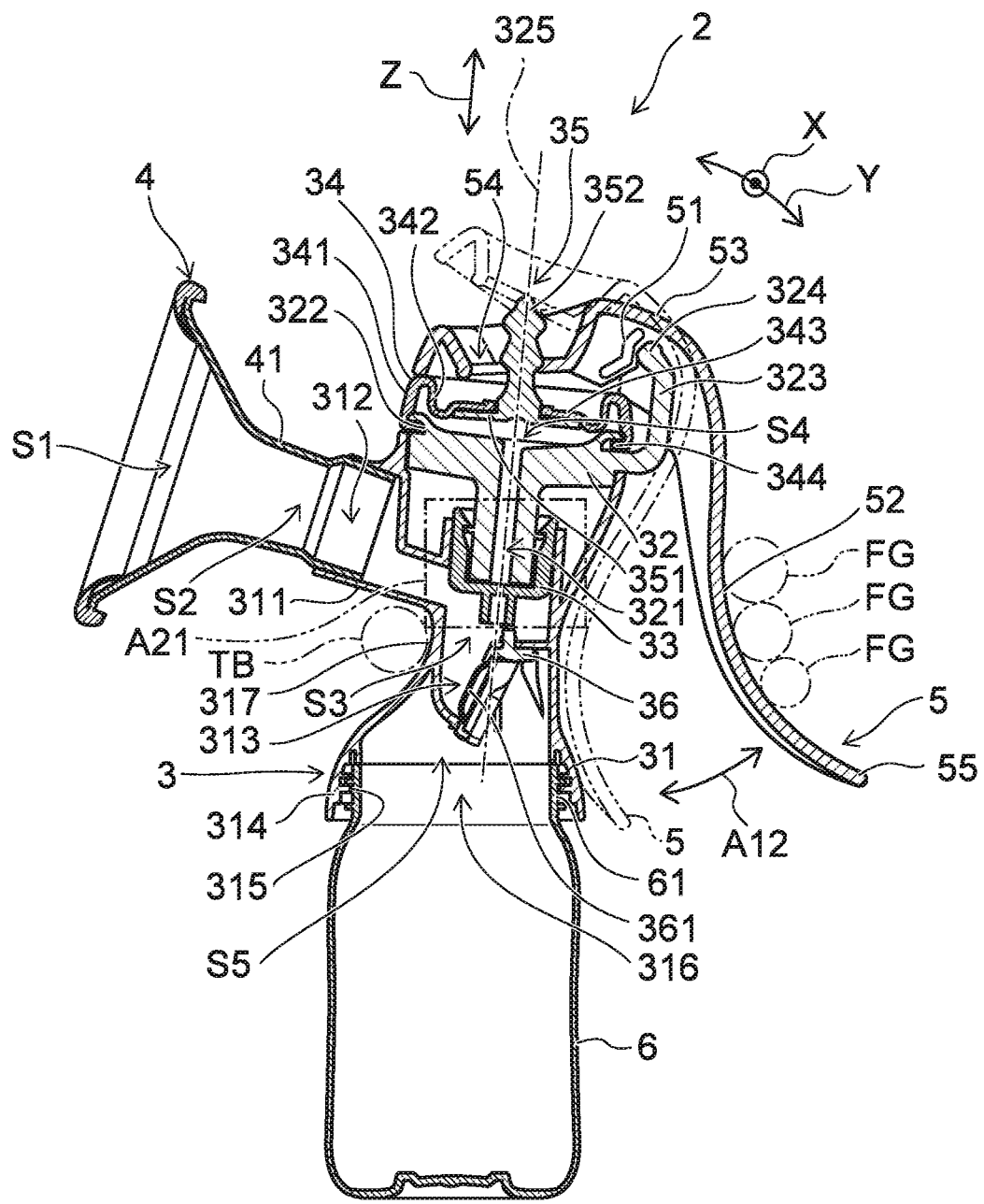
FIG. 2 is a cross-sectional view of an A1-A1 cross section illustrated in FIG. 1.

The main body 3 includes the casing 31, a base part 32, a holding member 33, a diaphragm 34, a coupler 35, and a check-valve 36. The casing 31 is molded of a relatively light and hard synthetic resin material. For example, polypropylene, polycarbonate, polycycloolefin, polyethersulfone, polyphenylsulfone, etc., are examples of the material of the casing 31. The mounting part 311 to which the hood 4 is mounted has a first passageway 312 through which a gas, the expressed breast milk, etc., pass. As illustrated in FIG. 2, the first passageway 312 spatially communicates with a communicating part S4 via an inner space S3 formed in a substantially central part inside the casing 31, a through-hole 335 (referring to FIG. 5 and FIG. 6B) of the holding member 33, and a second passageway 321 formed in the interior of the base part 32. The expressed breast milk is collected temporarily in the inner space S3.

The base part 32 is held by the casing 31 by means of the holding member 33, and has the communicating part S4 connected spatially to the inner space S3. The holding member 33 is provided at one of the casing 31 or the base part 32 and includes a wall part 332 sandwiched between the casing 31 and the base part 32 (referring to FIG. 5). The wall part 332 of the embodiment corresponds to the "wall part" of the invention. In the example illustrated in FIG. 2, the holding member 33 is provided at the base part 32. However, the holding member 33 may be provided at the casing 31. An example in which the holding member 33 is provided at the casing 31 is described below. The holding member 33 holds the base part 32 to the casing 31 and prevents gases and/or the breast milk from flowing through the gap between the casing 31 and the base part 32. In other words, the holding member 33 has a holding function of holding the base part 32 to the casing 31, and a sealing function of preventing gases and/or the breast milk from flowing through the gap between the casing 31 and the base part 32. For example, the holding member 33 is formed as one body from an elastic body of a synthetic resin, etc., and is flexible as an entirety. For example, silicone rubber, an elastomer, natural rubber or the like, etc., are examples of the material of the holding member 33. The details of the holding member 33 are described below.

The diaphragm 34 is provided at the upper part of the base part 32. For example, the diaphragm 34 is formed as one body from an elastic body of a synthetic resin, etc., and is flexible as an entirety. The diaphragm 34 is stretched to catch on the upper part of the base part 32 and to be connected to the upper part of the base part 32. Specifically, the diaphragm 34 is mounted to the base part 32 by a lower end part 344 of the diaphragm 34 catching on a groove part 322 provided in the upper part of the base part 32.

The base part 32 includes an arm 323 provided at a position on the side opposite to the mounting part 311. As illustrated in FIG. 2 and FIG. 4, the arm 323 passes between the diaphragm 34 and a notch 318 provided in the upper part of the casing 31 and extends to a position higher than the position where the diaphragm 34 is connected to the base part 32. Favorably, the arm 323 passes between the diaphragm 34 and the notch 318 of the casing 31 and extends to the position higher than the upper end of the diaphragm 34 at a position adjacent to the diaphragm 34.

A spindle part 324 which rotatably supports the handle 5 is formed at the upper end part of the arm 323. The spindle part 324 extends from the arm 323 along a width direction X of the handle 5 and is connected detachably at two end parts 324a and 324b to a pair of bearing parts 51 provided at the inner side of the handle 5. Thereby, as in arrow A11 illustrated in FIG. 1 and arrow A12 illustrated in FIG. 2, the handle 5 can rotate around the spindle part 324 (a Y-direction illustrated in FIG. 2) with the spindle part 324 of the base part 32 as the center. In other words, the casing 31 has a size which the user can grip with one hand. At the outer perimeter side surface at the hood 4 side as illustrated in FIG. 2, the casing 31 has a curved recess 317 to which a thumb TB can closely contact easily. In a state in which the thumb TB is placed on the recess 317, the user can touch any finger FG other than the thumb to a lever part 52 of the handle 5 and can simultaneously grip the casing 31 and the lever part 52 with one hand. Then, the user can perform the rotation operation of the handle 5 with the spindle part 324 as the center by clenching and relaxing the hand gripping the casing 31 and the lever part 52. The pivotally-supporting structure of the handle 5 is not limited thereto. For example, the bearing parts 51 of the handle 5 may be circular through-holes. In such a case, the spindle part 324 of the arm 323 passes through the bearing parts 51 which are through-holes.

The communicating part S4 which is formed between the base part 32 and the diaphragm 34 is a region (a space) where the negative pressure is applied. When the communicating part S4 which is formed between the base part 32 and the diaphragm 34 is set to a negative-pressure state due to the diaphragm 34 changing, the space S1 which is surrounded with the hood 4 is set to a negative-pressure state via the second passageway 321 of the base part 32, the through-hole 335 of the holding member 33, and the inner space S3 and the first passageway 312 of the casing 31.

The lower side of the inner space S3 of the casing 31 is open toward the bottle 6 via an opening 313. As illustrated in FIG. 2, the check-valve 36 is mounted detachably to the casing 31 at the portion where the opening 313 is formed. The check-valve 36 opens and closes the opening 313 formed in the interior of the casing 31 and prevents the backward flow of the breast milk passing through the opening 313. For example, the check-valve 36 is formed as one body from an elastic body of a synthetic resin, etc., and is flexible as an entirety. For example, silicone rubber, an elastomer, natural rubber or the like, etc., are examples of the material of the check-valve 36.

The check-valve 36 is pre-urged toward the casing 31 by its own elasticity and seals the opening 313 in the normal state (normally-closed). In other words, in the state of being mounted to the casing 31, the check-valve 36 is pressed toward the casing 31 by its own elasticity. That is, a bias in a direction toward the casing 31 is applied to the check-valve 36 by the elasticity of the check-valve 36.

When the communicating part S4 is set to a negative-pressure state, the inner space S3 of the casing 31 is set to a negative-pressure state via the second passageway 321 of the base part 32 and the through-hole 335 of the holding member 33. Then, a valve part 361 of the check-valve 36 is suctioned toward the inner space (the suction space) S3 via the opening 313 of the casing 31. Here, the valve part 361 includes a circular bottom part and has a dome configuration protruding toward the opening 313 from a base part connected to the periphery of the valve part 361. In other words, the distance between the center of the valve part 361 and the portion of the valve part 361 contacting the casing 31 (the peripheral portion of the valve part 361) is substantially the same over the entire periphery of the valve part 361. Therefore, a uniform force is applied to the valve part 361 in the state in which the valve part 361 seals the opening 313. In other words, in the state in which the valve part 361 seals the opening 313, the force on the valve part 361 from the casing 31 is uniform over the entire contact portion between the valve part 361 and the casing 31. Therefore, the occurrence of a gap between the valve part 361 and the casing 31 can be suppressed; and the dome-shaped valve part 361 can ensure higher sealability by being suctioned toward the inner space S3 via the opening 313.

When the negative-pressure state of the communicating part S4 is released and a prescribed amount of the expressed breast milk is collected at the region (the inner space S3) of the valve part 361 and the opening 313, the valve part 361 of the check-valve 36 opens the opening 313 due to the weight of the breast milk and/or the release of the negative pressure (the change of the pressure). Thereby, the expressed breast milk is guided into the interior of the bottle 6 via the opening 313.

The casing 31 includes a detachable part 314 at the lower end part of the casing 31 which is provided detachably on the bottle 6. The detachable part 314 has a dome configuration or a tubular configuration and has a space S5 communicating with the inner space S3 when the check-valve 36 opens the opening 313. An internal-thread part 315 is provided at the inner side of the detachable part 314. On the other hand, an external-thread part 61 is provided at the outer side of the upper end part of the bottle 6. The internal-thread part 315 of the detachable part 314 and the external-thread part 61 of the bottle 6 can screw together. The bottle 6 may be an exclusive part of the breast pump 2 or may be a nursing bottle suited to the detachable part 314, etc. Also, the bottle 6 may not be a molded container, and may have a bag configuration. The end part of the detachable part 314 of the embodiment has an opening 316 which corresponds to the bottle opening of any nursing bottle so that not only the bottle 6 which is an exclusive part of the breast pump 2 but also any nursing bottle can be attached and detached.

The diaphragm 34 is a negative-pressure generation member for generating a negative pressure. In the embodiment, the diaphragm 34 is connected to the upper part of the base part 32 and covers the communicating part S4. As illustrated in FIG. 2, the diaphragm 34 is bent complexly and has a sheet configuration resembling a relatively flat-bottomed circular tubular body as an entirety. Specifically, the diaphragm 34 includes a first wall part 341 which is upright at the outer side, and a second wall part 342 as an inner wall part where the upper end part is folded back inward as one body. The first wall part 341 has enough rigidity to maintain the outer diameter. The thickness of the second wall part 342 is thinner than the thickness of the first wall part 341. The second wall part 342 is provided as a deforming part. A bottom surface part 343 is connected to the lower end of the second wall part 342. The bottom surface part 343 is formed as one body with the second wall part 342 as a relatively wide inner bottom part and extends from the second wall part 342 toward the center to seal the circular tubular lower part. In other words, the first wall part 341 and the second wall part 342 are formed of the same material. Also, the first wall part 341 and the second wall part 342 are provided with mutually-different rigidities by setting the thicknesses of the material to be different from each other. Therefore, when the external force due to the operation of the handle 5 acts on the diaphragm 34, the second wall part 342 can deform even when the external force that acts is of a level at which the first wall part 341 would not deform.

The diaphragm 34 is formed of a relatively highly elastic flexible deforming material, i.e., a synthetic resin having a hardness of about HS 30 to 70 using a type-A durometer of JIS-K6253 (ISO 7619). For example, silicone rubber, isoprene rubber, an elastomer such as SEBS (styrene-ethylene-butylene-styrene) or the like, etc., are examples of the material of the diaphragm 34. In the embodiment, silicone rubber is utilized as the material of the diaphragm 34.

Favorably, the thickness of the material of the portion of the first wall part 341 is, for example, not less than about 1.5 mm and not more than about 3.0 mm. Specifically, the first wall part 341 of the diaphragm 34 extends downward and includes the lower end part 344 folded inward at the lower end. Similarly to the portion of the first wall part 341, the thickness of the lower end part 344 is, for example, not less than about 1.5 mm and not more than about 3.0 mm.

When the diaphragm 34 receives the action of the operation of the handle 5, the second wall part 342 deforms as the deforming part. Then, the volume of the space of the communicating part S4 formed between the bottom surface part 343 and the base part 32 changes. Thereby, the diaphragm 34 provides a constant amount of negative pressure to the communicating part S4. That is, the communicating part S4 changes to a negative-pressure state due to the deformation of the diaphragm 34. When the communicating part S4 changes to the negative-pressure state, the air inside the first passageway 312 is suctioned via the second passageway 321, the through-hole 335, and the inner space S3; and the breast milk is suctioned (expressed). At this time, the first wall part 341 substantially does not deform; and the connection state to the base part 32 is maintained. The diaphragm 34 of the embodiment includes the upright first wall part 341. Therefore, even if the height of the base part 32 is not very high, the diaphragm 34 can deform sufficiently above the base part 32 and can generate the necessary negative pressure in the communicating part S4.

The coupler 35 is provided in the diaphragm 34, is linked to the handle 5, and deforms the second wall part 342 of the diaphragm 34. The coupler 35 is formed of a hard material that is harder than the material of the second wall part 342 used as the deforming part. For example, synthetic resins such as polypropylene, polycarbonate, polycycloolefin, polyethersulfone, etc., are examples of the material of the coupler 35. The coupler 35 includes a flat disk-shaped base part 351. The base part 351 is disposed at the lower side (the communicating part S4 side) of the bottom surface part 343.

Also, the coupler 35 includes a linking part 352 protruding upward from the base part 351 and extending in an axis configuration. The linking part 352 is linked to the handle 5. Specifically, the linking part 352 is linkable to the handle 5 by being inserted through a through-hole (a hole having a smaller diameter than the base part 351) formed in the central part of the bottom surface part 343 of the diaphragm 34 and by being exposed at the upper side of the bottom surface part 343. The base part 351 pushes the bottom surface part 343 of the diaphragm 34 upward when the user pulls the handle 5 linked to the linking part 352 upward. Then, the second wall part 342 of the diaphragm 34 greatly deforms the space of the communicating part S4. The base part 351 of the embodiment is disposed at the lower side of the bottom surface part 343 of the diaphragm 34 without being connected to the bottom surface part 343. However, the mounting form of the base part 351 is not limited thereto. For example, the base part 351 may be fixed at the upper side of the bottom surface part 343.

As illustrated in FIG. 4, the linking part 352 includes a first protruding part 353 and a second protruding part 354 which are disposed to be arranged with each other in an extension direction Z of the linking part 352. The first protruding part 353 and the second protruding part 354 each protrude in a diametrically outward direction from the axial part of the linking part 352. A first engager 355 is provided between the first protruding part 353 and the second protruding part 354. The first engager 355 is a recessed portion (a groove portion) between the first protruding part 353 and the second protruding part 354. Also, a second engager 356 is provided between the second protruding part 354 and the base part 351. The second engager 356 is a recessed portion (a groove portion) between the second protruding part 354 and the base part 351.

The handle 5 is linked to the linking part 352 by engaging the first engager 355 or the second engager 356. The link position in the extension direction Z between the handle 5 and the linking part 352 is modifiable thereby. Therefore, the distance that the handle 5 pulls the linking part 352 upward is modifiable. The deformation amount of the diaphragm 34 can be modified thereby. In other words, as illustrated in FIG. 4, the first engager 355 and the second engager 356 are formed in stages to be separated from each other in the extension direction Z. Therefore, the distance that the handle 5 pulls the linking part 352 upward is modifiable in stages according to the engagement position between the handle 5 and the engagers 355 and 356.

The distance that the handle 5 pulls the linking part 352 upward is short when the handle 5 engages the first engager 355 compared to when the handle 5 engages the second engager 356. Then, the volume change of the space of the communicating part S4 is relatively small. Then, the handle 5 and the diaphragm 34 generate a relatively low negative pressure in the communicating part S4 and are restored to the original state in a relatively short period of time (a preparation mode). On the other hand, the distance that the handle 5 pulls the linking part 352 upward is long when the handle 5 engages the second engager 356 compared to when the handle 5 engages the first engager 355. Thereby, the volume change of the space of the communicating part S4 is relatively large. Thereby, the handle 5 and the diaphragm 34 generate a relatively high negative pressure in the communicating part S4 and are restored to the original state over a relatively long period of time (a breast milk expression mode).

The handle 5 has a long configuration and is molded as an entirety from a relatively hard and lightweight synthetic resin. For example, polypropylene, polycarbonate, polycycloolefin, polyethersulfone, etc., are examples of the material of the handle 5. The handle 5 includes a lift part 53 which is disposed above the diaphragm 34 and lifts the diaphragm 34 upward, and the lever part 52 which is bent from the lift part 53 and positioned at the side surface of the main body 3.

As illustrated in FIG. 3, a linked part 54 which is linked to the linking part 352 is provided in the lift part 53. The linked part 54 has a retaining opening 541 for retaining the link position of the linking part 352, and an insertion opening 542 for inserting the linking part 352. The retaining opening 541 and the insertion opening 542 are connected spatially to each other. The inner diameter of the retaining opening 541 is slightly larger than each of the outer diameters of the first engager 355 and the second engager 356, but is smaller than each of the outer diameters of the first protruding part 353 and the second protruding part 354. Conversely, the inner diameter of the insertion opening 542 is larger than each of the outer diameters of the first protruding part 353 and the second protruding part 354. Thereby, the user can align the handle 5 and the linking part 352 to each other by inserting the linking part 352 into the insertion opening 542 and subsequently sliding the linking part 352 toward the retaining opening 541 to insert the first engager 355 or the second engager 356 into the retaining opening 541.

The lever part 52 is formed in a lever configuration and performs the role of a hand hold. The outer region of the lever part 52 corresponds to a region where the user places the fingers FG other than the thumb. That is, the outer surface of the lever part 52 corresponds to a surface that the user touches with the fingers FG other than the thumb. The distance between the outer surface of the lever part 52 to which the user touches the fingers FG and the recess 317 where the user places the thumb TB is a distance such that the user can grip by squeezing the casing 31 between the recess 317 and the outer surface of the lever part 52. By the user clenching the hand which grips the casing 31 by squeezing, the lever part 52 is pressed toward the casing 31 and approaches the casing 31. Then, the handle 5 rotates with the spindle part 324 as the center. Then, the lift part 53 of the handle 5 lifts the diaphragm 34 upward by means of the coupler 35. Then, the volume of the space of the communicating part S4 enlarges and changes to a negative-pressure state. Thereby, the space S1 and the receiving space S2 which are surrounded with the hood 4 change to a negative-pressure state via the second passageway 321 of the base part 32, the through-hole 335 of the holding member 33, and the inner space S3 and the first passageway 312 of the casing 31. Thus, the expression of the breast milk is performed.

Downward from the region where the fingers FG are placed, the lever part 52 gradually curves outward. The appearance of a lower end part 55 of the handle 5 is slightly curled outward thereby. Therefore, the fingers FG can be suppressed from slipping toward the lower side of the handle 5 when the user causes the lever part 52 to approach the casing 31.

Here, for example, if the orientation of the handle with respect to the casing is fixed, the handle performs the back and forth motion of approaching and moving away from the casing in a state in which the orientation with respect to the casing is fixed. Therefore, in such a case, when the user expresses breast milk by using the breast pump, the orientation of the handle is determined necessarily when the hood is fitted to the breast. Then, there are cases where the user cannot place the joints of the hand operating the handle at an intermediate position. Therefore, there is room for improvement regarding the muscle load caused by the repeated operation of the handle.

Conversely, according to the breast pump 2 according to the embodiment, the casing 31 has the notch 318 as illustrated in FIG. 4. The notch 318 extends along the configuration of the end part of the casing 31 and is provided in the end part (in FIG. 4, the upper end part) of the casing 31 where the diaphragm 34 is connected. Then, the arm 323 of the base part 32 passes between the notch 318 and the diaphragm 34 and extends outside the casing 31. On the other hand, as illustrated in FIG. 2, the base part 32 is held by the casing 31 by interposing the holding member 33 which is mounted to the lower end part of the base part 32. That is, the base part 32 is provided as a member separate from the casing 31 and is not fixed to the casing 31. Therefore, the base part 32 can rotate with respect to the casing 31 with an axis 325 of the base part 32 as the center as in arrow Aly illustrated in FIG. 4. As described above, the handle 5 is connected to the spindle part 324 which is provided at the upper end part of the arm 323 of the base part 32. Therefore, as in arrow A13 and arrow A14 illustrated in FIG. 3A, the handle 5 can rotate with the base part 32 with respect to the casing 31 with the axis 325 of the base part 32 as the center. In other words, the base part 32 is connected to the handle 5 and rotates with the handle 5 with respect to the casing 31 by means of the holding member 33 when the handle 5 rotates with respect to the casing 31 with the axis 325 of the base part 32 as the center. Therefore, when fitting the hood 4 to the breast, the user can freely adjust the position (the angle) of the handle 5 with respect to the casing 31 and can place the joints of the hand operating the handle 5 at an intermediate position. The muscle load due to the repeated operation of the handle 5 can be reduced thereby.

Also, the base part 32 is provided as a member separate from the casing 31 and can rotate with respect to the casing 31 while being held by the casing 31 by means of the holding member 33. Therefore, a complex rotation mechanism rotating the handle 5 is unnecessary; and a circular tubular or cup-shaped member including a wall part having a height sufficient to surround the periphery of the space where the negative pressure is applied is unnecessary. Therefore, the internal structure of the breast pump 2 such as the section contacted by the breast milk, etc., can be simplified. Thereby, the user easily can clean the section contacted by the breast milk by disassembling the casing 31 and the base part 32 from each other.

As illustrated in FIG. 4, the casing 31 includes a regulator 319. The regulator 319 regulates the range of the rotation of the base part 32 with the axis 325 of the base part 32 as the center. Specifically, the regulator 319 includes a first stopper part 319a which is formed at one end part of the notch 318, and a second stopper part 319b which is formed at the end part of the notch 318. The first stopper part 319a and the second stopper part 319b correspond to wall parts formed at the two end parts of the notch 318. The rotation of the base part 32 stops when the base part 32 rotates and the arm 323 contacts one of the first stopper part 319a or the second stopper part 319b. In the example illustrated in FIG. 3B, the handle 5 which is connected to the base part 32 is stopped at a position rotated −45° from the state illustrated in FIG. 3A. Also, in the example illustrated in FIG. 3C, the handle 5 which is connected to the base part 32 is stopped at a position rotated 45° from the state illustrated in FIG. 3A. Thus, the range of the rotation of the handle 5 which rotates with the base part 32 is regulated by the regulator 319 of the casing 31. In other words, the range of the rotation of the handle 5 is limited to a prescribed range. Thereby, the range of the rotation of the handle 5 is clear; and the user can adjust the handle 5 with peace of mind to any position after ascertaining the rotation range of the handle 5.

Figure 5:
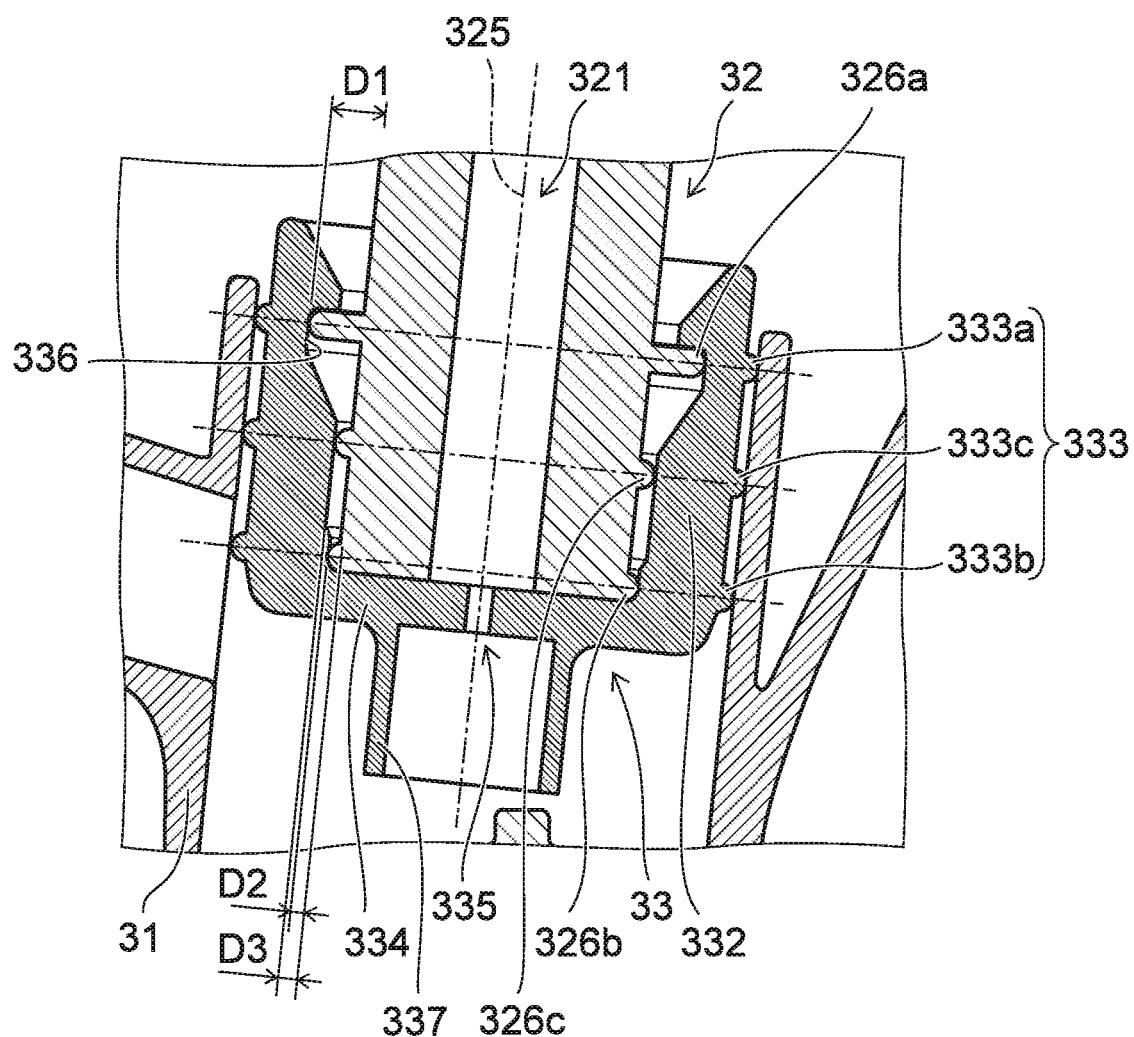
FIG. 5 is an enlarged view in which region A21 illustrated in FIG. 2 is enlarged.
Figure 6A:
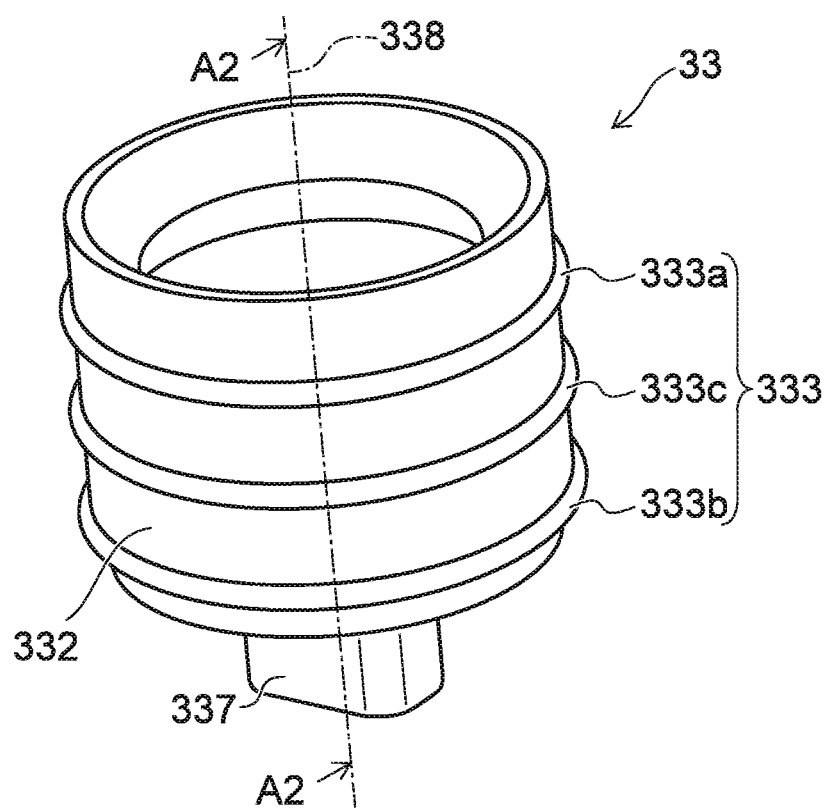
FIG. 6 is a drawing illustrating a holding member of the embodiment.
Figure 6B:
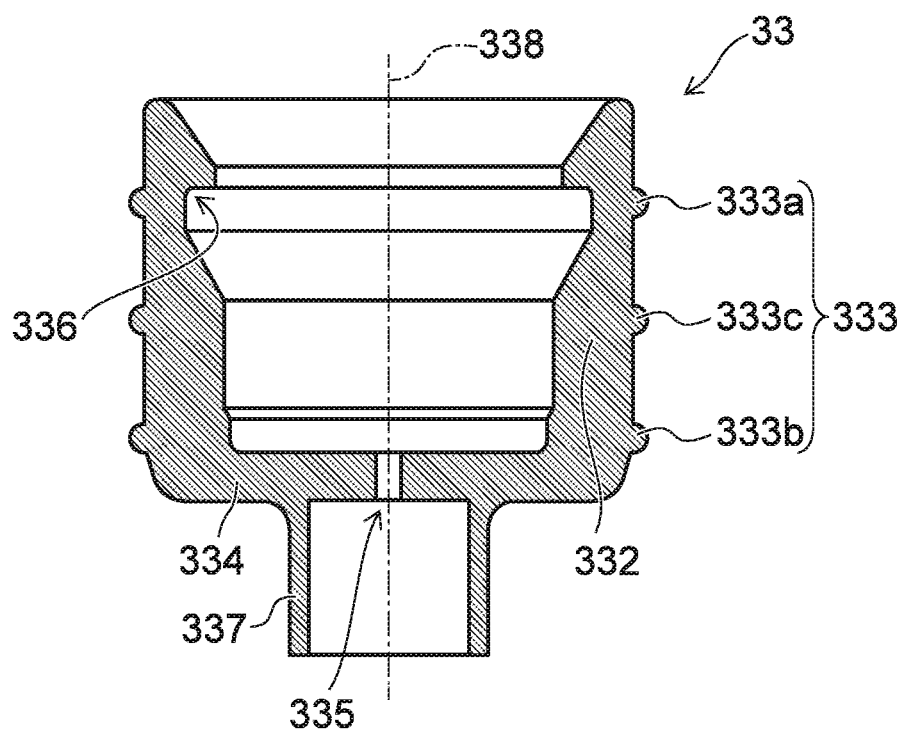

The state in which the base part 32 is held by the casing 31 by means of the holding member 33 will now be described in detail with reference to FIG. 5 to FIG. 7. As illustrated in FIG. 5, the holding member 33 is provided at the base part 32 and includes the wall part 332 sandwiched between the casing 31 and the base part 32. Also, the holding member 33 includes a bottom part 334, which is connected to the wall part 332 and extends inward. As illustrated in FIG. 6A and FIG. 6B, the holding member 33 is formed in a cup configuration or a tubular configuration. Also, the holding member 33 includes a holding structure 333 which supports the holding of the base part 32 by the casing 31. In other words, the holding structure 333 supports the holding of the base part 32 by the casing 31. The holding structure 333 protrudes outward from the outer surface of the wall part 332. In the state in which the wall part 332 of the holding member 33 is sandwiched between the casing 31 and the base part 32, the holding structure 333 protrudes from the outer surface of the wall part 332 toward the casing 31.

The holding structure 333 of the holding member 33 of the embodiment includes a first protrusion 333a, a second protrusion 333b, and a third protrusion 333c. The first protrusion 333a is formed as one body with the wall part 332 and extends in the circumferential direction of the wall part 332. That is, the first protrusion 333a is formed as one body with the wall part 332 and is provided in a ring configuration along the outer surface of the wall part 332. The second protrusion 333b is provided at a position separated from the first protrusion 333a in the direction of an axis 338 of the holding member 33. The second protrusion 333b is formed as one body with the wall part 332 and extends in the circumferential direction of the wall part 332. That is, the second protrusion 333b is formed as one body with the wall part 332 and is provided in a ring configuration along the outer surface of the wall part 332. The third protrusion 333c is provided between the first protrusion 333a and the second protrusion 333b. The third protrusion 333c is formed as one body with the wall part 332 and extends in the circumferential direction of the wall part 332. That is, the third protrusion 333c is formed as one body with the wall part 332 and is provided in a ring configuration along the outer surface of the wall part 332.

Thus, the first protrusion 333a, the second protrusion 333b, and the third protrusion 333c each protrude outward from the outer surface of the wall part 332 and are provided in ring configurations along the outer surface of the wall part 332. Therefore, in the state in which the base part 32 is held by the casing 31 by means of the holding member 33 (the state in which the wall part 332 is sandwiched between the casing 31 and the base part 32), the detachment of the holding member 33 from the casing 31 along the axis 325 of the base part 32 or along the axis 338 of the holding member 33 can be suppressed.

Thereby, for example, the detachment of the base part 32 from the casing 31 can be suppressed even when the force due to the operation of the handle 5 is applied in a direction oblique to the base part 32 connected to the handle 5. Also, the first protrusion 333a and the second protrusion 333b are provided to be separated from each other in the direction of the axis 338 of the holding member 33. Therefore, the first protrusion 333a and the second protrusion 333b can support the holding of the base part 32 by the casing 31 by receiving the force applied to the holding member 33 from the base part 32 at positions which are separated from each other. Thereby, for example, the detachment of the base part 32 from the casing 31 can be suppressed more reliably even when the force due to the operation of the handle 5 is applied in a direction oblique to the base part 32 connected to the handle 5. Further, the third protrusion 333c is provided between the first protrusion 333a and the second protrusion 333b. Therefore, the third protrusion 333c which is provided between the first protrusion 333a and the second protrusion 333b can ensure the sealability between the casing 31 and the base part 32 even when the force due to the operation of the handle 5 is applied in a direction oblique to the base part 32 connected to the handle 5.

In other words, the third protrusion 333c has a holding function of holding the base part 32 to the casing 31, and a sealing function of preventing a fluid from flowing through the gap between the casing 31 and the base part 32. As illustrated in FIG. 5, the first protrusion 333a of the embodiment contacts the casing 31 over the entire perimeter. Therefore, similarly to the third protrusion 333c, the first protrusion 333a has a holding function of holding the base part 32 to the casing 31, and a sealing function of preventing a fluid from flowing through the gap between the casing 31 and the base part 32. On the other hand, the second protrusion 333b of the embodiment includes a portion that partially does not contact the casing 31. Therefore, the second protrusion 333b has a holding function of holding the base part 32 to the casing 31.

Because the first protrusion 333a, the second protrusion 333b, and the third protrusion 333c each are provided in ring configurations along the outer surface of the wall part 332, the resistance force received from the casing 31 when the holding member 33 rotates with the axis 325 of the base part 32 or the axis 338 of the holding member 33 as the center is smaller than the resistance force received from the casing 31 when the holding member 33 moves along the axis 325 of the base part 32 or along the axis 338 of the holding member 33. Therefore, in the state in which the base part 32 is held by the casing 31 by means of the holding member 33 (the state in which the wall part 332 is sandwiched between the casing 31 and the base part 32), the holding member 33 can rotate with the axis 325 of the base part 32 or the axis 338 of the holding member 33 as the center while being suppressed from detaching from the casing 31. Thereby, when the handle 5 rotates with respect to the casing 31 with the axis 325 of the base part 32 as the center, the base part 32 at which the holding member 33 is provided can rotate with the handle 5 with respect to the casing 31 with the holding member 33 interposed in the state in which the base part 32 is held by the casing 31.

The first protrusion 333a, the second protrusion 333b, and the third protrusion 333c each are formed as one body with the wall part 332. Therefore, unlike an O-ring or the like provided as a member separate from the holding member, the first protrusion 333a, the second protrusion 333b, and the third protrusion 333c do not detach from the wall part 332 even when the holding member 33 receives a force aligned with the axis 325 of the base part 32 or the axis 338 of the holding member 33 and rotates with the axis 325 of the base part 32 or the axis 338 of the holding member 33 as the center. Therefore, the loss of the first protrusion 333a, the second protrusion 333b, and the third protrusion 333c can be suppressed.

Figure 7A:
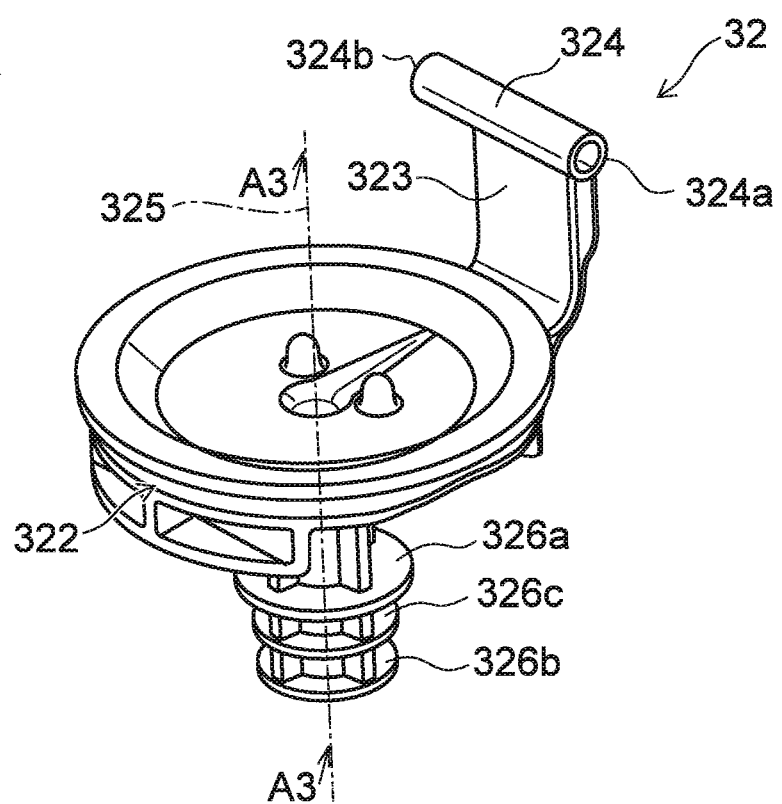
FIG. 7 is a drawing illustrating a base part of the embodiment.
Figure 7B:
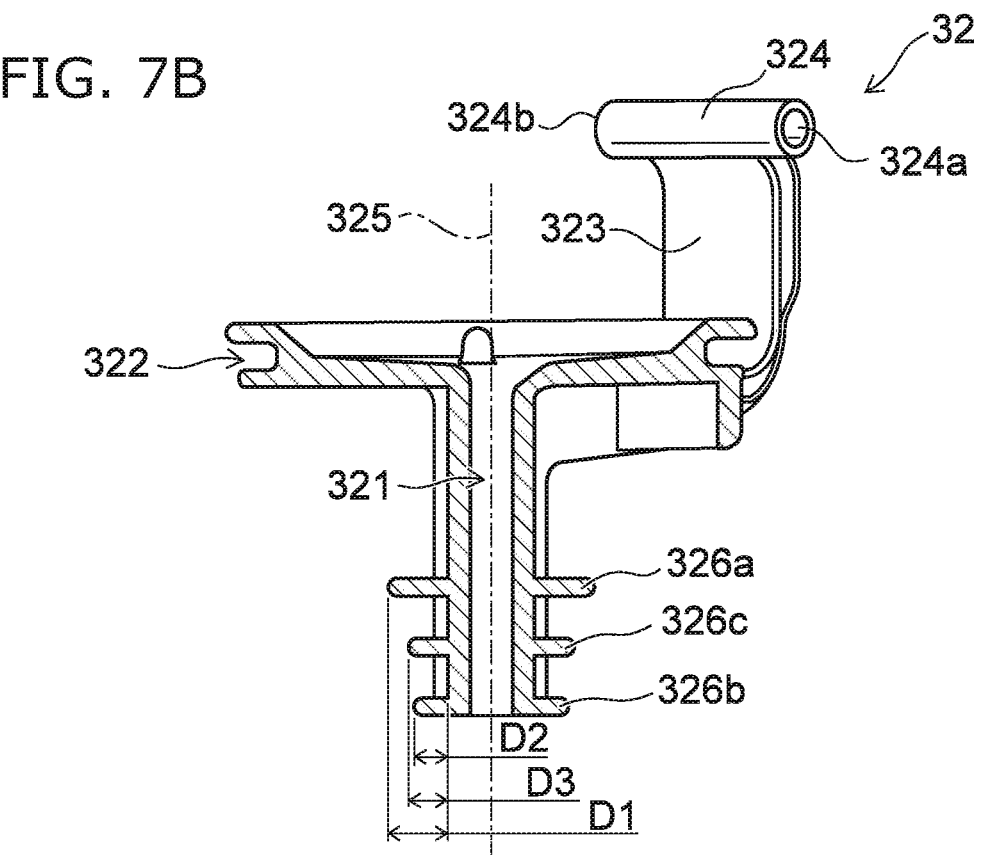

As illustrated in FIG. 5, FIG. 7A, and FIG. 7B, the base part 32 includes a first supporter 326a, a second supporter 326b, and a third supporter 326c. In the state in which the base part 32 is held by the casing 31 by means of the holding member 33, the first supporter 326a protrudes toward the first protrusion 333a and is provided at a position corresponding to the first protrusion 333a at the side opposite to the side where the first protrusion 333a protrudes. Therefore, the first supporter 326a can support the first protrusion 333a from the backside (the side opposite to the side where the first protrusion 333a protrudes) in the state in which the wall part 332 is sandwiched between the casing 31 and the base part 32. The second supporter 326b protrudes toward the second protrusion 333b and is provided at a position corresponding to the second protrusion 333b at the side opposite to the side where the second protrusion 333b protrudes. Therefore, the second supporter 326b can support the second protrusion 333b from the backside (the side opposite to the side where the second protrusion 333b protrudes) in the state in which the wall part 332 is sandwiched between the casing 31 and the base part 32. The third supporter 326c protrudes toward the third protrusion 333c and is provided at a position corresponding to the third protrusion 333c at the side opposite to the side where the third protrusion 333c protrudes. Therefore, the third supporter 326c can support the third protrusion 333c from the backside (the side opposite to the side where the third protrusion 333c protrudes) in the state in which the wall part 332 is sandwiched between the casing 31 and the base part 32. Thereby, the holding force of the base part 32 by the casing 31 can be increased; and the sealability between the casing 31 and the base part 32 can be increased.

A length D1 of the protrusion of the first supporter 326*a* (the protruding length of the first supporter 326*a*) is longer than a length D2 of the protrusion of the second supporter 326*b* (the protruding length of the second supporter 326*b*). The length D2 of the protrusion of the second supporter 326*b* is shorter than a length D3 of the protrusion of the third supporter 326*c* (the protruding length of the third supporter 326*c*). Thus, the protruding length D1 of the first supporter 326*a*, the protruding length D2 of the second supporter 326*b*, and the protruding length D3 of the third supporter 326*c* are different from each other. Therefore, the holding force of the base part 32 by the casing 31 can be appropriately adjusted; and the holding force can be suppressed from becoming excessively high. Thereby, the mutual disassembleability of the casing 31 and the base part 32 can be increased while maintaining the holding force of the base part 32 by the casing 31.

As illustrated in FIG. 5 and FIG. 6B, the holding member 33 includes a hook part 336. The hook part 336 is provided at the inner side of the wall part 332 and is formed as a groove part recessed from the inner surface of the wall part 332 toward the outer side of the wall part 332. Therefore, as illustrated in FIG. 5, at least one of the first supporter 326*a*, the second supporter 326*b*, or the third supporter 326*c* catches on the hook part 336. Therefore, the detachment of the holding member 33 from the base part 32 can be suppressed even when a relatively strong force is applied to the holding member 33.

Also, the holding member 33 includes a backflow prevention wall 337. The backflow prevention wall 337 surrounds the periphery of the through-hole 335 provided in the bottom part 334 of the holding member 33 and extends outward from the bottom part 334. The through-hole 335 spatially connects the inner space S3 and the communicating part S4. Therefore, the backflow prevention wall 337 can suppress the expressed breast milk from traveling along the wall part 332 and/or the bottom part 334 of the holding member 33 and being suctioned through the through-hole 335 toward the communicating part S4. That is, the backflow prevention wall 337 can suppress the flow (the backward flow) of the expressed breast milk via the through-hole 335 toward the communicating part S4.

When the handle 5 and the diaphragm 34 are restored to the original state and the negative-pressure state of the communicating part S4 is released, the speed at which the handle 5 is restored (the movement speed of the handle 5) changes according to, for example, the diameter of the through-hole 335 of the holding member 33, etc. Therefore, the movement speed of the handle 5 when the handle 5 is restored to the original state can be adjusted by adjusting the diameter of the through-hole 335 of the holding member 33. Thereby, the operative feel of the handle 5 can be improved; and the breast pump 2 can be provided with a luxurious feel.

A breast pump according to a first modification of the embodiment will now be described with reference to FIG. 8. A duplicate description is omitted as appropriate for components of the breast pump 2A according to the first modification similar to the components of the breast pump 2 described above in reference to FIG. 1 to FIG. 7; and the following description is focused on the differences.

In the breast pump 2A according to the first modification, a holding member 33A is provided at a casing 31A rather than at a base part 32A. The breast pump 2A according to the first modification differs from the breast pump 2 described above in reference to FIG. 1 to FIG. 7 in this regard.

The holding structure 333 of the modification protrudes inward from the inner surface of the wall part 332 of the holding member 33A. The holding structure 333 protrudes from the inner surface of the wall part 332 toward the base part 32A in the state in which the wall part 332 of the holding member 33A is sandwiched between the casing 31A and the base part 32A. The first protrusion 333*a*, the second protrusion 333*b*, and the third protrusion 333*c* each are formed as one body with the wall part 332 and are provided in ring configurations along the inner surface of the wall part 332. Therefore, the detachment of the base part 32A from the holding member 33A along the axis 325 of the base part 32A or along the axis 338 of the holding member 33A can be suppressed in the state in which the base part 32A is held by the casing 31A by means of the holding member 33A (the state in which the wall part 332 is sandwiched between the casing 31A and the base part 32A). Thereby, the detachment of the base part 32A from the casing 31A can be suppressed even when, for example, the force due to the operation of the handle 5 is applied in a direction oblique to the base part 32A connected to the handle 5.

The casing 31A includes a first supporter 371*a*, a second supporter 371*b*, and a third supporter 371*c*. In the state in which the base part 32A is held by the casing 31A by means of the holding member 33A, the first supporter 371*a* protrudes toward the first protrusion 333*a* and is provided at a position corresponding to the first protrusion 333*a* at the side opposite to the side where the first protrusion 333*a* protrudes. Therefore, the first supporter 371*a* can support the first protrusion 333*a* from the backside in the state in which the wall part 332 is sandwiched between the casing 31A and the base part 32A. The second supporter 371*b* protrudes toward the second protrusion 333*b* and is provided at a position corresponding to the second protrusion 333*b* at the side opposite to the side where the second protrusion 333*b* protrudes. Therefore, the second supporter 371*b* can support the second protrusion 333*b* from the backside in the state in which the wall part 332 is sandwiched between the casing 31A and the base part 32A. The third supporter 371*c* protrudes toward the third protrusion 333*c* and is provided at a position corresponding to the third protrusion 333*c* at the side opposite to the side where the third protrusion 333*c* protrudes. Therefore, the third supporter 371*c* can support the third protrusion 333*c* from the backside in the state in which the wall part 332 is sandwiched between the casing 31A and the base part 32A. Thereby, the holding force of the base part 32A to the casing 31A can be increased; and the sealability between the casing 31A and the base part 32A can be increased.

A length D4 of the protrusion of the first supporter 371*a* (the protruding length of the first supporter 371*a*) is longer than a length D5 of the protrusion of the second supporter 371*b* (the protruding length of the second supporter 371*b*). The length D5 of the protrusion of the second supporter 371*b* is shorter than a length D6 of the protrusion of the third supporter 371*c* (the protruding length of the third supporter 371*c*). Thus, the protruding length D4 of the first supporter 371*a*, the protruding length D5 of the second supporter 371*b*, and the protruding length D6 of the third supporter 371*c* are different from each other. Therefore, the holding force of the base part 32A to the casing 31A can be appropriately adjusted; and the holding force can be suppressed from becoming excessively high. Thereby, the mutual disassembleability of the casing 31A and the base part 32A can be increased while maintaining the holding force of the base part 32A to the casing 31A.

Figure 8:
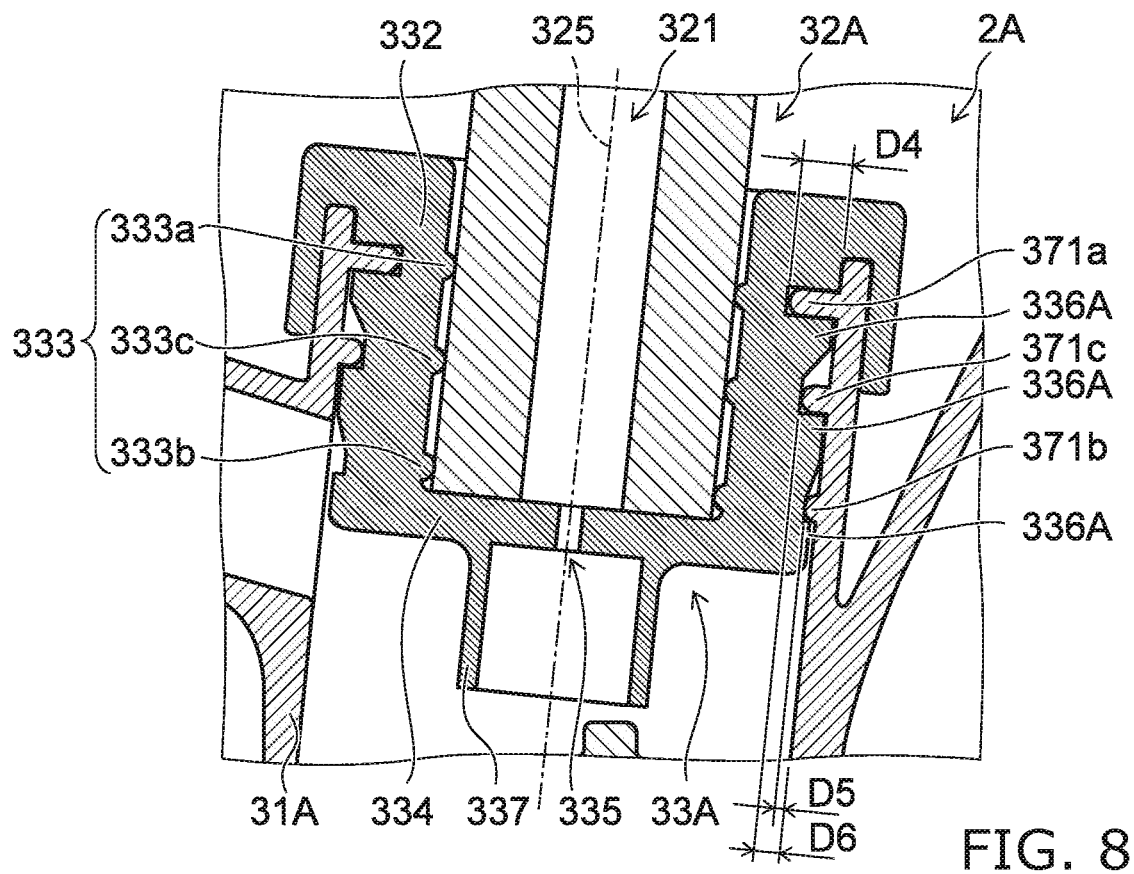
FIG. 8 is a cross-sectional view illustrating a manual breast pump according to a first modification of the embodiment.

As illustrated in FIG. 8, the holding member 33A includes a hook part 336A. The hook part 336A is provided at the outer side of the wall part 332 and is formed as a protrusion protruding from the outer surface of the wall part 332. Therefore, as illustrated in FIG. 8, the hook part 336A catches on at least one of the first supporter 371a, the second supporter 371b, or the third supporter 371c. Therefore, the detachment of the holding member 33A from the casing 31A can be suppressed even when a relatively strong force is applied to the holding member 33A.

A breast pump according to a second modification of the embodiment will now be described with reference to FIG. 9. A duplicate description is omitted as appropriate for components of the breast pump 2B according to the second modification similar to the components of the breast pump 2 described above in reference to FIG. 1 to FIG. 7; and the following description is focused on the differences.

In the breast pump 2B according to the second modification, a holding member 33B is provided at a casing 31B and not at a base part 32B. The breast pump 2B according to the second modification differs from the breast pump 2 described above in reference to FIG. 1 to FIG. 7 in this regard. Also, the base part 32B of the modification is held by the casing 31B by means of the holding member 33B by contacting the holding member 33B at the outer side of the holding member 33B and not at the inner side of the holding member 33B. The breast pump 2B according to the second modification differs from the breast pump 2A according to the first modification in this regard.

The holding structure 333 of the modification protrudes outward from the outer surface of the wall part 332 of the holding member 33B. The holding structure 333 of the modification is similar to the holding structure 333 of the holding member 33 described above in reference to FIG. 5 to FIG. 6B. As illustrated in FIG. 9, the first protrusion 333a, the second protrusion 333b, and the third protrusion 333c each contact the inner surface of the base part 32B. Therefore, the detachment of the base part 32B from the holding member 33B along the axis 325 of the base part 32B or the axis 338 of the holding member 33B can be suppressed in the state in which the base part 32B is held by the casing 31B by means of the holding member 33B (the state in which the wall part 332 is sandwiched between the casing 31B and the base part 32B). Thereby, the detachment of the base part 32B from the casing 31B can be suppressed even when, for example, the force due to the operation of the handle 5 is applied in a direction oblique to the base part 32B connected to the handle 5.

The casing 31B includes a first supporter 372a, a second supporter 372b, and a third supporter 372c. In the state in which the base part 32B is held by the casing 31B by means of the holding member 33B, the first supporter 372a protrudes toward the first protrusion 333a and is provided at a position corresponding to the first protrusion 333a at the side opposite to the side where the first protrusion 333a protrudes. Therefore, the first supporter 372a can support the first protrusion 333a from the backside in the state in which the wall part 332 is sandwiched between the casing 31B and the base part 32B. The second supporter 372b protrudes toward the second protrusion 333b and is provided at a position corresponding to the second protrusion 333b at the side opposite to the side where the second protrusion 333b protrudes. Therefore, the second supporter 372b can support the second protrusion 333b from the backside in the state in which the wall part 332 is sandwiched between the casing 31B and the base part 32B. The third supporter 372c protrudes toward the third protrusion 333c and is provided at a position corresponding to the third protrusion 333c at the side opposite to the side where the third protrusion 333c protrudes. Therefore, the third supporter 372c can support the third protrusion 333c from the backside in the state in which the wall part 332 is sandwiched between the casing 31B and the base part 32B. Thereby, the holding force of the base part 32B to the casing 31B can be increased; and the sealability between the casing 31B and the base part 32B can be increased.

A length D7 of the protrusion of the first supporter 372a (the protruding length of the first supporter 372a) is longer than a length D8 of the protrusion of the second supporter 372b (the protruding length of the second supporter 372b). The length D8 of the protrusion of the second supporter 372b is shorter than a length D9 of the protrusion of the third supporter 372c (the protruding length of the third supporter 372c). Thus, the protruding length D7 of the first supporter 372a, the protruding length D8 of the second supporter 372b, and the protruding length D9 of the third supporter 372c are different from each other. Therefore, the holding force of the base part 32B to the casing 31B can be appropriately adjusted; and the holding force can be suppressed from becoming excessively high. Thereby, the mutual disassembleability of the casing 31B and the base part 32B can be increased while maintaining the holding force of the base part 32B to the casing 31B.

Figure 9:
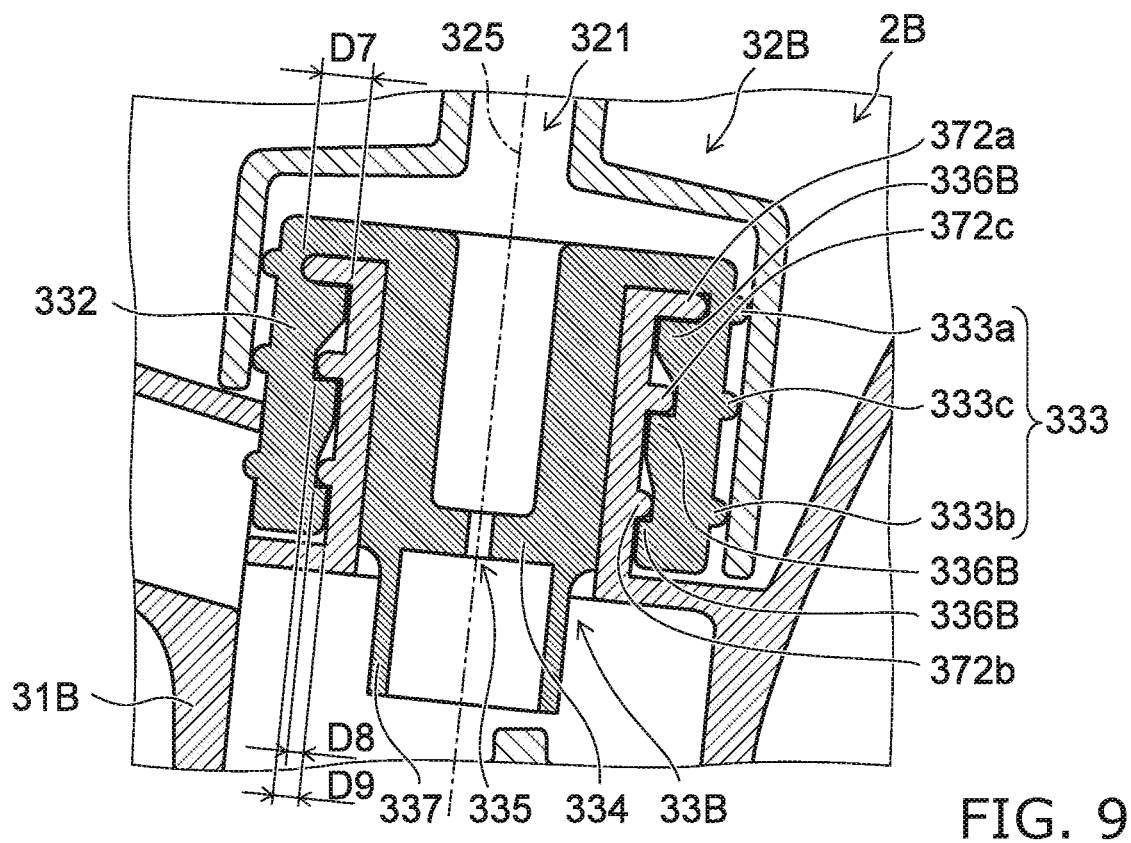
FIG. 9 is a cross-sectional view illustrating a manual breast pump according to a second modification of the embodiment.

As illustrated in FIG. 9, the holding member 33B includes a hook part 336B. The hook part 336B is provided at the inner side of the wall part 332 and is formed as a protrusion protruding from the inner surface of the wall part 332. Therefore, as illustrated in FIG. 9, the hook part 336B catches on at least one of the first supporter 372a, the second supporter 372b, or the third supporter 372c. Therefore, the detachment of the holding member 33B from the casing 31B can be suppressed even when a relatively strong force is applied to the holding member 33B.

An example of results of investigations performed by the inventor will now be described with reference to FIG. 10 and FIG. 11. The inventor performed investigations to quantitatively evaluate muscle activity. In other words, when the muscle fibers flex, a muscle potential is emitted as an action potential of the muscle fibers. It is generally known that the amplitude of the muscle potential changes substantially proportionally to the muscle output. Therefore, the muscle activity can be evaluated quantitatively by measuring the muscle potential.

The "MP150 system made by BIOPAC Systems" was used as the measuring device. The "sampling rate set by the measuring device when measuring" is 1000 samples/second. As the measurement conditions, the operation of clenching the handle 5 of the breast pump 2 to the maximum amount and subsequently releasing the handle 5 was repeated at a frequency of 2 times per 1 second. At this time, a load that is equivalent to the load when actually expressing breast milk was reproduced by plugging the breast milk expression port (the inlet of the hood 4) with a plug. As the measurement method (the analysis method), the effective value (RMS value: Root Mean Square value) was determined from the actual measured values of the muscle potential measured for 10 seconds. Also, the values (the relative values) of the effective values for handle angles respectively of −45°, −30°, −15°, +15°, +30°, and +45° divided by a reference value were determined using the effective value when the handle angle is 0° as the reference value (100%).

The "handle angle at 0°" refers to the state illustrated in FIG. 3A. The "sign of the handle angle being negative (−)" refers to the state illustrated in FIG. 3B. That is, the handle angle of the handle 5 illustrated in FIG. 3B is "−45°." On the other hand, the "sign of the handle angle being positive (+)"

refers to the state illustrated in FIG. 3C. That is, the handle angle of the handle 5 illustrated in FIG. 3C is "+45°."

Figure 10:
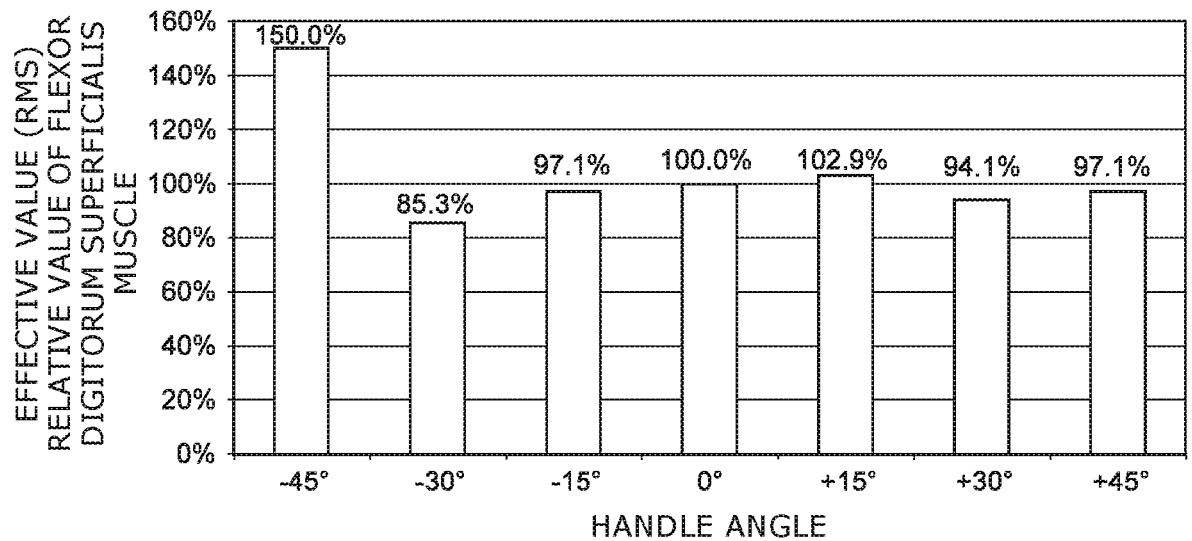
FIG. 10 is a graph illustrating the relationship between a handle angle and the relative value of the effective value of a flexor digitorum superficialis muscle.
Figure 11:
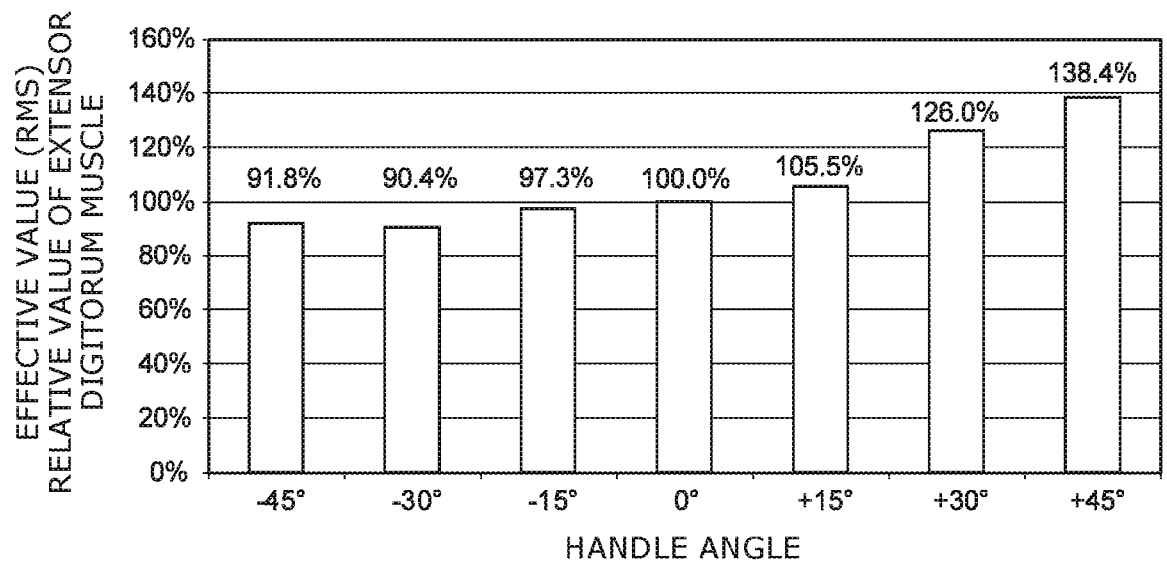
FIG. 11 is a graph illustrating the relationship between the handle angle and the relative value of the effective value of an extensor digitorum muscle.

An example of results of investigations performed by the inventor are as illustrated in FIG. 10 and FIG. 11. Namely, an example of the relationship between the handle angle and the relative value of the effective value of the flexor digitorum superficialis muscle is as illustrated in FIG. 10. Also, an example of the relationship between the handle angle and the relative value of the effective value of the extensor digitorum muscle is as illustrated in FIG. 11. The flexor digitorum superficialis muscle is one type of muscle existing in the upper limb of a human and mainly functions in the operation of clenching the handle 5, etc., and in the operation of causing palmar flexion of the hand joint. Also, the extensor digitorum muscle is one type of muscle existing in the upper limb of a human and mainly functions in the operation of releasing the handle 5, etc., and in the operation of causing dorsal flexion of the hand joint.

According to the graphs illustrated in FIG. 10 and FIG. 11, it is shown that the effective values of the flexor digitorum superficialis muscle and the extensor digitorum muscle when the handle angle is −15° and −30° is smaller than the effective value (the reference value) when the handle angle is 0°. It is also shown that when the handle angle is −30°, a breast milk expression operation equivalent to the breast milk expression operation when the handle angle is 0° is possible using a muscle activity amount of about 85 to 90% of that when the handle angle is 0°. Thereby, this suggests that the muscle load can be reduced by appropriately adjusting the position (the angle) of the handle 5.

Hereinabove, embodiments of the invention are described. However, the invention is not limited to the embodiments recited above; and various modifications can be performed without departing from the scope of the claims. The configurations of the embodiments recited above can be partially omitted; and arbitrary combinations different from those recited above are possible.

REFERENCE NUMERAL LIST 2, 2A, 2B breast pumps
3 main body
4 hood
5 handle
6 bottle
31, 31A, 31B casings
32, 32A, 32B base parts
33, 33A, 33B holding members
34 diaphragm
35 coupler
36 check-valve
41 reduced-diameter part
51 bearing part
52 lever part
53 lift part
54 linked part
55 lower end part
61 external-thread part
311 mounting part
312 first passageway
313 opening
314 detachable part
315 internal-thread part
316 opening
317 recess
318 notch
319 regulator
319a first stopper part
319b second stopper part
321 second passageway
322 groove part
323 arm
324 spindle part
324a, 324b end parts
325 axis
326a first supporter
326b second supporter
326c third supporter
332 wall part
333 holding structure
333a first protrusion
333b second protrusion
333c third protrusion
334 bottom part
335 through-hole
336, 336A, 336B hook parts
337 backflow prevention wall
338 axis
341 first wall part
342 second wall part
343 bottom surface part
344 lower end part
351 base part
352 linking part
353 first protruding part
354 second protruding part
355 first engager
356 second engager
361 valve part
371a first supporter
371b second supporter
371c third supporter
372a first supporter
372b second supporter
372c third supporter
541 holding opening
542 insertion opening
FG finger
S1 space
S2 receiving space
S3 inner space
S4 communicating part
S5 space
TB thumb

The invention claimed is:

1. A manual breast pump, comprising:
a main body casing having an inner space where breast milk is collected temporarily;
a hood connected to the main body casing and configured to be fitted to a breast;
a base part having a tubular shape extending in an axis of the base part, the base part having a circular outer circumference and a hollow thereinside, and is held by the main body casing and has a communicating part connected spatially to the inner space;
a diaphragm generating a negative pressure in the communicating part and being provided at the base part;
a holding member including a wall part that extends in the axis of the base part, the holding member including a circular inner circumference and a circular outer circumference wherein the wall part is sandwiched between the main body casing and the base part to be held; and a handle which is connected to the base part, is provided to be rotatable with respect to the main body casing around the axis of the base part as a center, and is for an operation of deforming the diaphragm, wherein the holding member has a holding structure that includes a first protrusion and a second protrusion wherein the first protrusion and the second protrusion protrude from the outer circumference of the wall part in a radial direction with respect to the axis of the base part, extending in a circumferential direction of the wall part such that the first protrusion and the second protrusion are in a ring shape surrounding the outer circumference of the wall part, and the second protrusion is distant from the first protrusion in an axial direction along the axis of the base part, the base part including a first supporter and a second supporter wherein the first supporter and the second supporter protrude from the circular outer circumference of the base part in the radial direction with respect to the axis of the base part, extending in the circumferential direction of the base part such that the first supporter and the second supporter are in a ring shape surrounding the outer circumference of the base part, the first supporter being provided at a position corresponding to the first protrusion such that the first supporter and the first protrusion are aligned in the radial direction, the second supporter being provided at a position corresponding to the second protrusion such that the second supporter and the second protrusion are aligned in the radial direction, and a protruding length of the first supporter being longer than a protruding length of the second supporter, the holding member including a hook part that is a recess formed on the circular inner circumference of the wall part at the position corresponding to the first supporter such that the first supporter is fit in the hook part while the base part is held with the wall part, preventing the base part from detaching from the wall part, when the handle rotates with respect to the main body casing around the axis of the base part as the center, the base part rotates with the handle with respect to the main body casing with the holding member interposed, the holding member formed from an elastic body and being flexible as an entirety, the base part held by the wall part and a gap between the main body casing and the base part sealed by the wall part, wherein the holding member has a through-hole which connects the communicating part spatially to the inner space, the base part having a passageway that is formed protrusively toward the holding member, and the holding member formed in either a cup shape or a tubular shape, and structured to accommodate the passageway in an interior of the holding member.

2. The manual breast pump according to claim 1, wherein the main body casing includes a regulator regulating a range of rotating of the base part with the axis of the base part as the center.

3. The manual breast pump according to claim 1, wherein the holding member has the holding structure protruding from a surface of the wall part toward one of the main body casing or the base part and supporting a holding of the base part by the main body casing.

4. The manual breast pump according to claim 1, wherein the holding member further includes a third protrusion wherein the third protrusion protrudes from the outer circumference of the wall part in the radial direction with respect to the axis of the base part and extends in the circumferential direction of the wall part such that the third protrusion is in the ring shape surrounding the outer circumference of the wall part, and is provided between the first protrusion and the second protrusion, the second protrusion positioned closer to the inner space.

5. The manual breast pump according to claim 4, wherein the base part includes a third supporter, wherein the third supporter protrudes from the outer circumference of the base part in the radial direction with respect to the axis of the base part and extending in the circumferential direction of the base part such that the third supporter is in the ring shape surrounding the outer circumference of the base part, the third supporter provided at a position corresponding to the third protrusion such that the third supporter and the third protrusion are aligned in the radial direction, a protruding length of the third supporter being longer than the protruding length of the second supporter and shorter than the protruding length of the first supporter.

6. The manual breast pump according to claim 1, wherein the holding member includes:
a bottom part having the through-hole; and
a backflow prevention wall surrounding a periphery of the through-hole and extending outward from the bottom part.

7. The manual breast pump according to claim 1, wherein an inner diameter of the wall part is larger than an outer diameter of the communicating part, and
an inner diameter of the through-hole is smaller than an inner diameter of the communicating part.

8. The manual breast pump according to claim 1, wherein the first protrusion and the second protrusion are integrally formed with the wall part, and
the first supporter and the second supporter are integrally formed with the base part.

9. A manual breast pump, comprising:
a main body casing having an inner space where breast milk is collected temporarily;
a hood connected to the main body casing and configured to be fitted to a breast;
a base part having a tubular shape extending in an axis of the base part, the base part having a circular outer circumference and a hollow thereinside, and is held by the main body casing and has a communicating part connected spatially to the inner space;
a diaphragm generating a negative pressure in the communicating part and being provided at the base part;
a holding member including a wall part that extends in the axis of the base part, the holding member including a circular inner circumference and a circular outer circumference wherein the wall part is sandwiched between the main body casing and the base part to be held; and
a handle which is connected to the base part, is provided to be rotatable with respect to the main body casing around the axis of the base part as a center, and is for an operation of deforming the diaphragm, wherein the holding member has a holding structure that includes a first protrusion, a second protrusion, and a third protrusion wherein the first protrusion, the second protrusion, and the third protrusion protrude from the circular outer circumference of the wall part in a radial direction with respect to the axis of the base part, extending in a circumferential direction of the wall part such that the first protrusion, the second protrusion, and the third protrusion are formed in a ring shape surrounding the outer circumference of the wall part, the second protrusion is distant from the first protrusion in an axial direction along the axis of the base part, and the third protrusion is provided between the first protrusion and the second protrusion, the base part including a first supporter, a second supporter, and a third supporter wherein the first supporter, the second supporter, and the third supporter protrude from the outer circumference of the base part in the radial direction with respect to the axis of the base part, extending in the circumferential direction of the base part such that the first supporter, the second supporter, and the third supporter are formed in the ring shape surrounding the outer circumference of the base part, the first supporter being provided at a position corresponding to the first protrusion such that the first supporter and the first protrusion are aligned in the radial direction, the second supporter being provided at a position corresponding to the second protrusion such that the second supporter and the second protrusion are aligned in the radial direction, and the third supporter being provided at a position corresponding to the third protrusion such that the third supporter and the third protrusion are aligned in the radial direction, and the holding member including a hook part that is a recess formed on the circular inner circumference of the wall part such that one of the first supporter, the second supporter, and the third supporter is fit in the hook part while the base part is held with the wall part, preventing the base part from detaching from the wall part, a protruding length of the first supporter is longer than a protruding length of the second supporter, and a protruding length of the third supporter is longer than the protruding length of the second supporter and shorter than the protruding length of the first supporter to prevent a holding force of the base part by the casing from being excessively high, when the handle rotates with respect to the main body casing around the axis of the base part as the center, the base part rotates with the handle with respect to the main body casing with the holding member interposed, the holding member formed from an elastic body and being flexible as an entirety, the base part held by the wall part and a gap between the main body casing and the base part sealed by the wall part, wherein the holding member has a through-hole which connects the communicating part spatially to the inner space, the base part having a passageway that is formed protrusively toward the holding member, and the holding member formed in either a cup shape or a tubular shape, and structured to accommodate the passageway in an interior of the holding member.

10. The manual breast pump according to claim 9, wherein the holding member includes:

a bottom part having the through-hole; and a backflow prevention wall surrounding a periphery of the through-hole and extending outward from the bottom part.

11. The manual breast pump according to claim 9, wherein an inner diameter of the wall part is larger than an outer diameter of the communicating part, and an inner diameter of the through-hole is smaller than an inner diameter of the communicating part.

12. The manual breast pump according to claim 9, wherein the first protrusion and the second protrusion are integrally formed with the wall part, and the first supporter and the second supporter are integrally formed with the base part.

\* \* \* \* \*